United States Patent
McNicol et al.

(10) Patent No.: US 9,872,885 B2
(45) Date of Patent: *Jan. 23, 2018

(54) ANTIMICROBIAL AND ANTI-INFLAMMATORY PEPTIDES

(71) Applicant: CARRUS CAPITAL CORPORATION, Vancouver (CA)

(72) Inventors: Patricia J. McNicol, Vancouver (CA); Sonia K. Pawlak, Vancouver (CA); Evelina Rubinchik, Richmond (CA); Dale Cameron, Richmond (CA); Maria Marta Guarna, Vancouver (CA); Janet R. Fraser, Vancouver (CA); Shafique Fidai, North Vancouver (CA); Yuchen Chen, Chapel Hill, NC (US); Timothy J. Krieger, Lowell, MA (US)

(73) Assignee: CARRUS CAPITAL CORPORATION (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/573,120

(22) Filed: Dec. 17, 2014

(65) Prior Publication Data

US 2015/0343015 A1 Dec. 3, 2015

Related U.S. Application Data

(62) Division of application No. 10/229,368, filed on Aug. 26, 2002, now Pat. No. 8,933,029.

(60) Provisional application No. 60/315,003, filed on Aug. 24, 2001.

(51) Int. Cl.
| | |
|---|---|
| *A61K 38/04* | (2006.01) |
| *A61K 38/10* | (2006.01) |
| *A61K 45/06* | (2006.01) |
| *C07K 7/08* | (2006.01) |
| *A61K 38/00* | (2006.01) |

(52) U.S. Cl.
CPC .............. *A61K 38/10* (2013.01); *A61K 45/06* (2013.01); *C07K 7/08* (2013.01); *A61K 38/00* (2013.01)

(58) Field of Classification Search
None
See application file for complete search history.

(56) References Cited

U.S. PATENT DOCUMENTS

| | | |
|---|---|---|
| 4,816,449 A | 3/1989 | Hahn |
| 5,324,716 A | 6/1994 | Selsted et al. |
| 5,359,030 A | 10/1994 | Ekwuribe |
| 5,409,898 A | 4/1995 | Darveau et al. |
| 5,436,222 A | 7/1995 | Kuna et al. |
| 5,438,040 A | 8/1995 | Ekwuribe |
| 5,505,949 A | 4/1996 | Benitez |
| 5,523,288 A | 6/1996 | Cohen et al. |
| 5,547,939 A | 8/1996 | Selsted |
| 5,593,866 A | 1/1997 | Hancock et al. |
| 5,679,665 A | 10/1997 | Bergamini et al. |
| 5,776,892 A | 7/1998 | Counts et al. |
| 5,834,430 A | 11/1998 | Porro et al. |
| 6,177,471 B1 | 1/2001 | Menander et al. |
| 6,180,604 B1 | 1/2001 | Fraser |
| 6,190,691 B1 | 2/2001 | Mak |
| 6,191,254 B1 | 2/2001 | Falla et al. |
| 6,248,343 B1 | 6/2001 | Jampani et al. |
| RE37,263 E | 7/2001 | Kross et al. |
| 6,482,799 B1 | 11/2002 | Tuse et al. |
| 6,503,881 B2 | 1/2003 | Krieger et al. |
| 6,538,106 B1 | 3/2003 | Fraser et al. |
| 8,138,144 B2 | 3/2012 | Krieger et al. |
| 8,202,835 B2 | 6/2012 | Hillman |
| 8,227,406 B2 | 7/2012 | Schmidtchen et al. |
| 8,426,366 B2 | 4/2013 | Hillman et al. |
| 8,466,102 B2 | 6/2013 | Krieger et al. |
| 8,927,487 B2* | 1/2015 | Krieger .................. A61K 38/10 514/2.3 |
| 8,933,029 B2* | 1/2015 | McNicol ................ A61K 45/06 424/184.1 |
| 9,227,999 B2* | 1/2016 | Krieger .................. A61K 38/10 |
| 9,248,928 B2* | 2/2016 | Rogers ................. A61K 9/0048 |
| 2002/0035061 A1 | 3/2002 | Krieger et al. |
| 2003/0148945 A1* | 8/2003 | McNicol ................ A61K 45/06 514/2.1 |

(Continued)

FOREIGN PATENT DOCUMENTS

| | | |
|---|---|---|
| EP | 0930065 | 9/2004 |
| WO | WO-9112815 | 9/1991 |

(Continued)

OTHER PUBLICATIONS

Metlitskaia et al, Biotechnol. Appl. Biochem. (2004) 39, 339-345.*
Lijuan Zhang & Timothy J Falla (2004) Cationic antimicrobial peptides—an update, Expert Opinion on Investigational Drugs, 13:2, 97-106.*
Boman, "Innate immunity and the normal microflora," Immunological Reviews 173:5-16 (2000).
Braegger, "Immunopathogenesis of chronic inflammatory bowel disease," Acta Paediatrica, 83(395):18-21 (1994).
Buku, "Mast cell degranulating (MCD) peptide: a prototypic peptide in allergy and inflammation," Peptides, 20(3):415-420 (1999).

(Continued)

*Primary Examiner* — Nita M. Minnifield
(74) *Attorney, Agent, or Firm* — Foley & Lardner LLP; Karen Mangasarian; Gitanjali Chimalakonda

(57) ABSTRACT

Antimicrobial and/or anti-inflammatory peptide compositions and therapeutic uses thereof are provided. The peptides and analogs or derivatives thereof may be used as an antimicrobial agent and/or as an anti-inflammatory agent. In certain embodiments, the peptides are cationic peptides. The peptides are useful for the treatment of inflammatory diseases, such as microorganism-caused infections, acne, and psoriasis. The peptides and peptide formulations may be used topically or parenterally.

27 Claims, 2 Drawing Sheets

(56) References Cited

U.S. PATENT DOCUMENTS

| | | | | |
|---|---|---|---|---|
| 2003/0219854 | A1* | 11/2003 | Guarna | C07K 14/001 435/68.1 |
| 2013/0296227 | A1* | 11/2013 | Krieger | A61K 38/10 514/2.4 |
| 2015/0087580 | A1* | 3/2015 | Krieger | A61K 38/10 514/2.4 |
| 2015/0343015 | A1* | 12/2015 | McNicol | A61K 45/06 514/12.2 |

FOREIGN PATENT DOCUMENTS

| | | |
|---|---|---|
| WO | WO-9215286 | 9/1992 |
| WO | WO-9324513 | 12/1993 |
| WO | WO-9704796 | 2/1997 |
| WO | WO-9731942 | 9/1997 |
| WO | WO-9807745 | 2/1998 |
| WO | WO-9840401 | 9/1998 |
| WO | WO-9943357 | 9/1999 |
| WO | WO-9958141 | 11/1999 |
| WO | WO-9965506 | 12/1999 |
| WO | WO-0071175 | 11/2000 |
| WO | WO-03015809 | 2/2003 |

OTHER PUBLICATIONS

Burkhart et al., "Acne: a review of immunologic and micobiologic factors," Postgrad Medical Journal, 75(884):328-331 (1999).
Chaly et al., "Neutrophil alpha-defensin human neutrophil peptide modulates cytokine production in human monocytes and adhesion molecule expression in endothelial cells.," European Cytokine Network, 11(2): 257-266 (2000).
Cole et al., "Human antimicrobial peptides: analysis and application," Biotechniques, 29(4):822-831 (2000).
Creighton, Protein Structure: A Practical Approach, 184-186 (1989).
Creighton, Proteins: Structures and Molecular Properties, 314-315 (1984).
Cruse and Lewis, Illustrated Dictionary of Immunology, Second Edition, CRC Press 2003.
Cutuli et al., "Antimicrobial effects of alpha-MSH peptides," Journal of Leukocyte Biology, 67(2):233-239 (2000).
Dahlberg et al., "A novel endotoxin antagonist attenuates tumor necrosis factor-alpha secretion," Journal of Surgical Research, 63(1):44-48 (1996).
Dankesreiter et at, "Synthetic endotoxin-binding peptides block endotoxin-triggered TNF-alpha production by macrophages in vitro and in vivo and prevent endotoxin-mediated toxic shock," Journal of Immunology, 164(9):4804-4811 (2000).
Dorland's online Medical Dictionary.
Ek et al., "Tachykinins and Calcitonin Gene-Related Peptide in Oxazolone-Induced Allergic Contact dermatitis in Mice," Journal of Investigative Dermatology 94(6):79-117 (1996).
Epand et al., "Diversity of antimicrobial peptides and their mechanisms of action," Biochimica et Biophysica Acta, 1462(102):11-28 (1999).
European Office Action dated Apr. 7, 2009 for corresponding European Application No. 02762161.4 (4 pages).
Falla et al., "Mode of action of the antimicrobial peptide indolicidin," Journal of Biological Chemistry 271 (32):19298-19303 (1996).
Falla et al., "Improved activity of a synthetic indolicidin analog," Antimicrobial Agents and Chemotherapy, 41(4):771-775 (1997).
Fox, Biotechnology, 12 (1994).
Fox et al., "A novel urease-negative *Helicobacter* species associated with colitis and typhlitis in IL-10-deficient mice," Infection and Immunity, 67(4):1757-1762 (1999).
Goebeler et al., "Substance P and calcitonin gene-related peptide modulate leukocyte infiltration to mouse skin during allergic contact dermatitis," Archives of Dermatological Research, 286(6):341-346 (1994).

Gough et al, "Antiendotoxin activity of cationic peptide antimicrobial agents," Infection and Immunity 64(12): 4922-4927 (1996).
Gu et al., "Synthesis and characterization of lipooligosaccharide-based conjugates as vaccine candidates for Moraxella (Branhamella) catarrhalis," Infection and Immunity, 66(5):1891-1897 (1998).
Guenther et al., "A comparison of tazarotene 0.1% gel once daily plus mometasone furoate 0.1% cream once daily versus calcipotriene 0.005% ointment twice daily in the treatment of plaque psoriasis," Clinical Therapeutics, 22(10):1225-1238 (2000).
Gutwald et al., "Neuropeptides enhance irritant and allergic contact dermatitis," *Journal of Investigative Dermatology* 96(5) :695-698 (1991).
Hancock, "The role of fundamental research and biotechnology in finding solutions to the global problem of antibiotic resistance," Clinical Infectious Diseases, 24(Supp 1):S148-S150 (1997).
Hancock et al., "The role of cationic antimicrobial peptides in innate host defenses," Trends in Microbiology 8(9):402-410 (2000).
Hancock et al., "The role of antimicrobial peptides in animal defenses," PNAS, 97(16):8856-8861 (2000).
Hancock et al., "Cationic peptides: a new source of antibiotics," Trends in Microbiology, 16(2): 82-8 (1998).
Haworth et al., "Anti-inflammatory activity of c(ILDV-NH($CH_2$)$_5$CO), a novel, selective, cyclic peptide inhibitor of VLA-4-mediated cell adhesion," *British Journal of Pharmacology*, 126(8):1751-1760 (1999).
Hiltz et al., "Alpha-MSH peptides inhibit acute inflammation and contact sensitivity," *Peptides* 11(5):979-982 (1990).
Hogasen et al., "Polymyxin B stimulates production of complement components and cytokines in human monocytes," Antimicrobial Agents and Chemotherapy 39(2):529-532 (1995).
Kyd et al., "Investigation of mucosal immunisation in pulmonary clearance of Moraxella (Branhamella) catarrhalis," Vaccine, 18(5-6):398-406 (2000).
Lawyer et al, "Antimicrobial activity of a 13 amino acid tryptophan-rich peptide derived from a putative porcine precursor protein of a novel family of antibacterial peptides," FEBS Letters, 390(1):95-98 (1996).
Lipton et al., "Central Administration of the Peptide a-MSH Inhibits Inflammation in the Skin," *Peptides* 12(4):795-798 (1991).
Lloret et al., "In vitro and in vivo effects of the anti-inflammatory peptides, antiflammins" Biochemical Pharmacology 44(7):1437-1441 (1992).
Lloret et al., "Effects of an anti-inflammatory peptide (antiflammin 2) on cell influx, eicosanoid biosynthesis and oedema formation by arachidonic acid and tetradecanoyl phorbol dermal application," Biochemical Pharmacology 50(3):347-353 (1995).
Luger et al., "Cutaneous immunomodulation and coordination of skin stress responses by alpha-melanocyte-stimulating hormone," *Annals of the New York Academy of Sciences*, 840:381-394 (1998).
Maki., "Pathogenesis, Prevention, and Management of Infections Due to Intravascular Devices Used for Infusion Therapy," in Infections Associated with Indwelling Medical Devices, (Bisna and Waldvogel, eds.), pp. 161.177, Washington D.C.: American Society for Microbiology (1989).
Masera et al., "Corticostatins/defensins inhibit in vitro NK activity and cytokine production by human peripheral blood mononuclear cells," Regulatory Peptides, 62(1):13-21 (1996).
McNicol et al., Abstract Interscience Conference Antimicrobiology Agents Chemotherapy, Dec. 16-19, 2001, Abstract No. F-349.
Nosoh et al., Protein Stability and Stabilization Through Engineering, chapter 7, p. 197, second paragraph (1991).
Odeh, "The role of tumour necrosis factor-alpha in the pathogenesis of complicated falciparum malaria," Cytokine, 14(1)11-18 (2001).
Olsen, "Therapy of acne," Medical Clinics of North America, 66(4):851-871 (1982).
Paulus et al., "Nonsteroid anti-inflammatory agents," Annual Review of Pharmacology, 13:107-125 (1973).
Rheins et al., "Alpha-melanocyte stimulating hormone modulates contact hypersensitivity responsiveness in C57/BL6 mice," Journal of Investigative Dermatology, 93(4):511-517 (1989).

(56) References Cited

OTHER PUBLICATIONS

Robinson et al., "Anti-HIV-1 activity of indolicidin, an antimicrobial peptide from neutrophils," Journal of Leukocyte Biology, 63(1):94-100 (1998).
Roszkowski et al, "Suppression of cell-mediated immune reactivity by peptides cleaved from human fibrinogen," Upsala Journal of Medical Sciences, 90(3):279-291 (1985).
Samukawa et al "Immune response to surface protein A of *Streptococcus pneumoniae* and to high-molecular-weight outer membrane protein A of Moraxella catarrhalis in children with acute otitis media," Journal of Infectious Diseases, 181(5):1842-1845 (2000).
Sartor, Current Concepts of the Etiology and Pathogenesis of Ulcerative Colitis and Crohn's Disease, Gasreoenterology Clinic of North America, 24:475-507 (1995).
Scott et al., "Biological Properties of Structurally Related a-Helical Cationic Antimicrobial Peptides," Infection and Immunity, 67(4): 2005-2009 (1999).
Scott et al., "Interaction of Cationic Peptides with Lipoteichoic Acid and Gram-Positive Bacteria," Infection and Immunity, 67(12): 6445-6453 (1999).
Scott et al., "Cationic antimicrobial peptides and their multifunctional role in the immune system," Critical Reviews in Immunology, 20(5):407-431 (2000).
Scott et al., "Cutting Edge: Cationic Antimicrobial Peptides Block the Binding of Lipopolysaccharide (LPS) to LPS Binding Protein." Journal of Immunology,164: 549-553, 2000.
Scott et al., "An α-Helical Cationic Antimicrobial Peptide Selectively Modulates Macrophage Responses to Lipopolysaccharide and Directly Alters Macrophage Gene Expression," Journal of Immunology, 165:3358-3365 (2000).
Selsted et al., "Indolicidin, a novel bactericidal tridecapeptide amide from neutrophils," Journal of Biological Chemistry, 267(7):4292-4295 (1992).
Selsted et al., "Purification, characterization, synthesis and cDNA cloning of indolicidin: A tryptophan-rich microbicidal tridecapeptide from neutrophils," pp. 905-907, Proceedings of the 12th American Peptide Symposium, Jun. 16-21, 1991, Cambridge, MA.
Shi et at, "PR-39, a proline-rich antibacterial peptide that inhibits phagocyte NADPH oxidase activity by binding to Src homology 3 domains of p47 phox," PNAS, 93(12):6014-6018 (1996).

Shkenderov, S., "New Pharmacobiochemical Data on the Anti-Inflammatory Effect of Bee Venom, in Animal, Plant, and Microbial Toxins," vol. 2 (A. Ohsada, K. Hayashi and Y. Sawai, eds), pp. 319-336, New York: Plenum (1976).
Sigusch et al., "Early-Onset and Adult Periodontitis Associated with Abnormal Cytokine Production by Activated T Lymphocytes," Journal of Periodontology 69(10): 1098-1104 (1998).
Somerfield et al., "Bee venom melittin blocks neutrophil $O_2$-production," Inflammation, 10(2):175-182 (1986).
Subbalakshmi et al., "Mechanism of antimicrobial action of indolicidin," FEMS Microbiology Letters, 160(1):91-96 (1998).
Subbalakshmi et al., "Requirements for antibacterial and hemolytic activities in the bovine neutrophil derived 13-residue peptide indolicidin," FEBS Letters, 395(1): 48-52 (1996).
Van Abel et al., "Synthesis and characterization of indolicidin, a tryptophan-rich antimicrobial peptide from bovine neutrophils," International Journal of Peptide and Protein Research, 45(5):401-409 (1995).
Van Wetering et al., "Defensins: key players or bystanders in infection, injury, and repair in the lung?," Journal of Allergy and Clinical Immunology, 104(6):1131-1138 (1999).
Van Wetering et al., "Effect of defensins on interleukin-8 synthesis in airway epithelial cells," American Journal of Physiology, 272(5 Pt 1):L888-896 (1997).
Vowels et al, "Induction of Proinflammatory Cytokines by a Soluble Factor of Propionibacterium acnes: Implications for Chronic Inflammatory Acne," Infection and Immunity, 63(8): 3158-3165 (1995).
Webester's II New Riverside University Dictionary, The Riverside Publishing Company 1984.
Wei et al., "Anti-inflammatory peptide agonists.," Annual Review of Pharmacology and Toxicology, 33:91-108 (1993).
Wright et al., "An animal model for external ear canal inflammation," Laryngoscope, 110(7):1112-1118 (2000).
Young et al., "Tachyphylaxis in 12-0-Tetradecanoylphorbol Acetate- and Arachidonic Acid-Induced Ear Edema," Journal of Investigative Dermatology 80:48-52 (1983).
Zunic et al., "MDP(Lysyl)GDP, a nontoxic muramyl dipeptide derivative, inhibits cytokine production by activated macrophages and protects mice from phorbol ester- and oxazolone-induced inflammation," Journal of Investigative Dermatology, 111(1):77-82 (1998).

* cited by examiner

SEQUENCE LISTING

<160> NUMBER OF SEQ ID NOS: 140

<210> SEQ ID NO 1
<211> LENGTH: 18
<212> TYPE: PRT
<213> ORGANISM: Artificial Sequence
<220> FEATURE:
<223> OTHER INFORMATION: Indolicidin peptide analogs

<400> SEQUENCE: 1

Gly Asn Asn Arg Pro Val Tyr Ile Pro Gln Pro Arg Pro Pro His Pro
 1               5                  10                  15

Arg Ile

<210> SEQ ID NO 2
<211> LENGTH: 25
<212> TYPE: PRT
<213> ORGANISM: Artificial Sequence
<220> FEATURE:
<223> OTHER INFORMATION: Indolicidin peptide analogs

<400> SEQUENCE: 2

Lys Lys Ala Ala Ala Lys Ala Ala Ala Ala Lys Ala Ala Trp Ala
 1               5                  10                  15

Ala Lys Ala Ala Ala Lys Lys Lys Lys
            20                  25

<210> SEQ ID NO 3
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 3

Ile Leu Pro Trp Lys Trp Pro Trp Trp Pro Trp Arg Arg
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 4

Ile Leu Pro Trp Lys Trp Pro Trp Trp Pro Trp Arg Arg
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 5

Ile Leu Lys Lys Trp Pro Trp Trp Pro Trp Arg Arg Lys
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 6

Ile Leu Lys Lys Trp Pro Trp Trp Pro Trp Arg Arg Lys
 1               5                  10

<210> SEQ ID NO 7
<211> LENGTH: 13

```
<212> TYPE: PRT
<213> ORGANISM: Artificial Sequence
<220> FEATURE:
<223> OTHER INFORMATION: Indolicidin peptide analogs

<400> SEQUENCE: 7

Lys Arg Arg Trp Pro Trp Trp Pro Trp Lys Lys Leu Ile
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 8

Ile Leu Lys Lys Phe Pro Phe Phe Pro Phe Arg Arg Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 9

Ile Leu Lys Lys Ile Pro Ile Ile Pro Ile Arg Arg Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 10

Ile Leu Lys Lys Tyr Pro Tyr Tyr Pro Tyr Arg Arg Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 11

Ile Leu Lys Lys Trp Pro Trp Pro Trp Arg Arg Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 12

Ile Leu Lys Lys Tyr Pro Trp Tyr Pro Trp Arg Arg Lys
1               5                   10

<210> SEQ ID NO 13
<211> LENGTH: 13
<212> TYPE: PRT
```

```
<213> ORGANISM: Artificial Sequence
<220> FEATURE:
<223> OTHER INFORMATION: Indolicidin peptide analogs

<400> SEQUENCE: 13

Ile Leu Lys Lys Phe Pro Trp Phe Pro Trp Arg Arg Lys
 1               5                  10

<210> SEQ ID NO 14
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 14

Ile Leu Lys Lys Phe Pro Phe Trp Pro Trp Arg Arg Lys
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 15

Ile Leu Arg Tyr Val Tyr Tyr Val Tyr Arg Arg Lys
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Indolicidin peptide analogs

<400> SEQUENCE: 16

Ile Leu Arg Trp Pro Trp Trp Pro Trp Trp Pro Trp Arg Arg Lys
 1               5                  10                  15

<210> SEQ ID NO 17
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 17

Trp Trp Arg Trp Pro Trp Trp Pro Trp Arg Arg Lys
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 18

Ile Leu Arg Arg Trp Pro Trp Trp Pro Trp Arg Arg Lys
 1               5                  10

<210> SEQ ID NO 19
<211> LENGTH: 12
<212> TYPE: PRT
<213> ORGANISM: Artificial Sequence
```

<220> FEATURE:
<223> OTHER INFORMATION: Indolicidin peptide analogs

<400> SEQUENCE: 19

Ile Leu Arg Arg Trp Pro Trp Trp Pro Trp Arg Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 20

Ile Leu Lys Trp Pro Trp Trp Pro Trp Arg Arg Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 21

Ile Leu Lys Lys Trp Pro Trp Trp Pro Trp Arg Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 22

Ile Leu Lys Trp Pro Trp Trp Pro Trp Arg Lys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 23

Ile Leu Arg Trp Pro Trp Trp Pro Trp Arg Arg Lys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 24

Lys Arg Arg Trp Pro Trp Trp Pro Trp Arg Leu Ile
1               5                   10

<210> SEQ ID NO 25
<211> LENGTH: 11
<212> TYPE: PRT
<213> ORGANISM: Artificial Sequence
<220> FEATURE:

<223> OTHER INFORMATION: Indolicidin peptide analogs

<400> SEQUENCE: 25

Ile Leu Trp Pro Trp Trp Pro Trp Arg Arg Lys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 26

Ile Leu Arg Arg Trp Pro Trp Trp Pro Trp Arg Arg Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 27

Ile Leu Lys Lys Trp Pro Trp Trp Pro Trp Lys Lys Lys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 28

Ile Leu Glu Glu Trp Pro Trp Trp Pro Trp Glu Glu Glu
1               5                   10

<210> SEQ ID NO 29
<211> LENGTH: 21
<212> TYPE: PRT
<213> ORGANISM: Artificial Sequence
<220> FEATURE:
<223> OTHER INFORMATION: Indolicidin peptide analogs

<400> SEQUENCE: 29

Ile Leu Arg Trp Pro Trp Trp Pro Trp Arg Arg Lys Ile Met Ile Leu
1               5                   10                  15

Lys Lys Ala Gly Ser
            20

<210> SEQ ID NO 30
<211> LENGTH: 20
<212> TYPE: PRT
<213> ORGANISM: Artificial Sequence
<220> FEATURE:
<223> OTHER INFORMATION: Indolicidin peptide analogs

<400> SEQUENCE: 30

Ile Leu Arg Trp Pro Trp Trp Pro Trp Arg Arg Lys Met Ile Leu Lys
1               5                   10                  15

Lys Ala Gly Ser
            20

```
<210> SEQ ID NO 31
<211> LENGTH: 21
<212> TYPE: PRT
<213> ORGANISM: Artificial Sequence
<220> FEATURE:
<223> OTHER INFORMATION: Indolicidin peptide analogs

<400> SEQUENCE: 31

Ile Leu Arg Trp Pro Trp Trp Pro Trp Arg Arg Lys Asp Met Ile Leu
1               5                   10                  15

Lys Lys Ala Gly Ser
            20

<210> SEQ ID NO 32
<211> LENGTH: 14
<212> TYPE: PRT
<213> ORGANISM: Artificial Sequence
<220> FEATURE:
<223> OTHER INFORMATION: Indolicidin peptide analogs

<400> SEQUENCE: 32

Ile Leu Arg Trp Pro Trp Arg Arg Trp Pro Trp Arg Arg Lys
1               5                   10

<210> SEQ ID NO 33
<211> LENGTH: 28
<212> TYPE: PRT
<213> ORGANISM: Artificial Sequence
<220> FEATURE:
<223> OTHER INFORMATION: Indolicidin peptide analogs

<400> SEQUENCE: 33

Ile Leu Arg Trp Pro Trp Trp Pro Trp Arg Arg Lys Ile Leu Met Arg
1               5                   10                  15

Trp Pro Trp Trp Pro Trp Arg Arg Lys Met Ala Ala
            20                  25

<210> SEQ ID NO 34
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 34

Ile Leu Thr Trp Pro Trp Trp Pro Trp Thr Thr Thr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 35

Lys Arg Lys Trp Pro Trp Trp Pro Trp Arg Leu Ile
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 36
```

Ile Leu Lys Trp Val Trp Trp Val Trp Arg Arg Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 37

Ile Leu Gln Trp Pro Trp Trp Pro Trp Gln Gln Gln
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 38

Ile Leu Lys Lys Trp Ala Trp Trp Pro Trp Arg Arg Lys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 39

Ile Leu Lys Lys Trp Pro Trp Trp Ala Trp Arg Arg Lys
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 40

Trp Trp Lys Lys Trp Pro Trp Trp Pro Trp Arg Arg Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 41

Leu Lys Lys Trp Pro Trp Trp Pro Trp Arg Arg Lys
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Indolicidin peptide analogs

<400> SEQUENCE: 42

Pro Trp Trp Pro Trp Arg Arg Lys
1               5

<210> SEQ ID NO 43
<211> LENGTH: 21
<212> TYPE: PRT
<213> ORGANISM: Artificial Sequence
<220> FEATURE:
<223> OTHER INFORMATION: Indolicidin peptide analogs

<400> SEQUENCE: 43

Ile Leu Lys Lys Trp Pro Trp Trp Pro Trp Arg Arg Lys Met Ile Leu
1               5                   10                  15

Lys Lys Ala Gly Ser
            20

<210> SEQ ID NO 44
<211> LENGTH: 20
<212> TYPE: PRT
<213> ORGANISM: Artificial Sequence
<220> FEATURE:
<223> OTHER INFORMATION: Indolicidin peptide analogs

<400> SEQUENCE: 44

Ile Leu Lys Lys Trp Pro Trp Trp Pro Trp Arg Arg Met Ile Leu Lys
1               5                   10                  15

Lys Ala Gly Ser
            20

<210> SEQ ID NO 45
<211> LENGTH: 21
<212> TYPE: PRT
<213> ORGANISM: Artificial Sequence
<220> FEATURE:
<223> OTHER INFORMATION: Indolicidin peptide analogs

<400> SEQUENCE: 45

Ile Leu Lys Lys Trp Pro Trp Trp Pro Trp Arg Arg Ile Met Ile Leu
1               5                   10                  15

Lys Lys Ala Gly Ser
            20

<210> SEQ ID NO 46
<211> LENGTH: 7
<212> TYPE: PRT
<213> ORGANISM: Artificial Sequence
<220> FEATURE:
<223> OTHER INFORMATION: Indolicidin peptide analogs

<400> SEQUENCE: 46

Trp Trp Pro Trp Arg Arg Lys
1               5

<210> SEQ ID NO 47
<211> LENGTH: 7
<212> TYPE: PRT
<213> ORGANISM: Artificial Sequence
<220> FEATURE:
<223> OTHER INFORMATION: Indolicidin peptide analogs

<400> SEQUENCE: 47

Ile Leu Lys Lys Trp Pro Trp
1               5

<210> SEQ ID NO 48

```
<211> LENGTH: 14
<212> TYPE: PRT
<213> ORGANISM: Artificial Sequence
<220> FEATURE:
<223> OTHER INFORMATION: Indolicidin peptide analogs

<400> SEQUENCE: 48

Ile Leu Lys Lys Trp Pro Trp Trp Pro Trp Arg Arg Lys Met
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 49

Ile Leu Lys Lys Trp Pro Trp Trp Pro Trp Arg Arg Met
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Indolicidin peptide analogs

<400> SEQUENCE: 50

Ile Leu Lys Lys Trp Pro Trp Trp Pro Trp Arg Arg Ile Met
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 51

Ile Leu Lys Lys Trp Trp Trp Pro Trp Arg Lys
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 52

Ile Leu Lys Lys Trp Pro Trp Trp Arg Lys
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 53

Trp Arg Ile Trp Lys Pro Lys Trp Arg Leu Pro Lys Trp
1               5                   10

<210> SEQ ID NO 54
<211> LENGTH: 12
```

```
<212> TYPE: PRT
<213> ORGANISM: Artificial Sequence
<220> FEATURE:
<223> OTHER INFORMATION: Indolicidin peptide analogs

<400> SEQUENCE: 54

Cys Leu Arg Trp Pro Trp Trp Pro Trp Arg Arg Lys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 55

Ile Leu Arg Trp Pro Trp Trp Pro Trp Arg Arg Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (1)...(1)
<223> OTHER INFORMATION: D-Isoleucine

<400> SEQUENCE: 56

Ile Leu Lys Lys Trp Pro Trp Trp Pro Trp Arg Arg Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (13)...(13)
<223> OTHER INFORMATION: D-Lysine

<400> SEQUENCE: 57

Ile Leu Lys Lys Trp Pro Trp Trp Pro Trp Arg Arg Lys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (1)...(1)
<223> OTHER INFORMATION: D-Isoleucine
<220> FEATURE:
<221> NAME/KEY: MOD_RES
<222> LOCATION: (13)...(13)
<223> OTHER INFORMATION: D-Lysine

<400> SEQUENCE: 58

Ile Leu Lys Lys Trp Pro Trp Trp Pro Trp Arg Arg Lys
1               5                   10
```

```
<210> SEQ ID NO 59
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 59

Ile Leu Lys Lys Trp Val Trp Trp Val Trp Arg Arg Lys
 1               5                  10

<210> SEQ ID NO 60
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 60

Ile Leu Lys Lys Trp Pro Trp Trp Val Trp Arg Arg Lys
 1               5                  10

<210> SEQ ID NO 61
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 61

Ile Leu Lys Lys Trp Val Trp Trp Pro Trp Arg Arg Lys
 1               5                  10

<210> SEQ ID NO 62
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 62

Ile Leu Arg Trp Val Trp Trp Val Trp Arg Arg Lys
 1               5                  10

<210> SEQ ID NO 63
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 63

Lys Arg Arg Trp Val Trp Trp Val Trp Arg Leu Ile
 1               5                  10

<210> SEQ ID NO 64
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 64

Ile Leu Arg Arg Trp Val Trp Trp Val Trp Arg Arg Lys
 1               5                  10

<210> SEQ ID NO 65
```

```
<211> LENGTH: 14
<212> TYPE: PRT
<213> ORGANISM: Artificial Sequence
<220> FEATURE:
<223> OTHER INFORMATION: Indolicidin peptide analogs

<400> SEQUENCE: 65

Ile Leu Arg Trp Trp Val Trp Trp Val Trp Trp Arg Arg Lys
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Indolicidin peptide analogs

<400> SEQUENCE: 66

Arg Leu Trp Val Trp Trp Val Trp
1               5

<210> SEQ ID NO 67
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 67

Arg Leu Trp Val Trp Trp Val Trp Arg Arg Lys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 68

Arg Leu Trp Val Trp Trp Val Trp Arg Arg
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 69

Arg Leu Gly Gly Gly Trp Val Trp Trp Val Trp Arg Arg
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 70

Arg Leu Trp Trp Val Val Trp Trp Arg Arg
1               5                   10

<210> SEQ ID NO 71
<211> LENGTH: 10
```

```
<212> TYPE: PRT
<213> ORGANISM: Artificial Sequence
<220> FEATURE:
<223> OTHER INFORMATION: Indolicidin peptide analogs

<400> SEQUENCE: 71

Arg Leu Trp Trp Gln Gln Trp Trp Arg Arg
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 72

Arg Leu Val Val Trp Trp Val Val Arg Arg
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 73

Arg Leu Phe Val Trp Trp Val Phe Arg Arg
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 74

Arg Leu Trp Val Val Val Val Trp Arg Arg
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 75

Arg Leu Val Val Trp Val Val Trp Arg Arg
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (1)...(1)
<223> OTHER INFORMATION: D-Arginine

<400> SEQUENCE: 76

Arg Leu Trp Val Trp Trp Val Trp Arg Arg
1               5                   10
```

<210> SEQ ID NO 77
<211> LENGTH: 10
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (10)...(10)
<223> OTHER INFORMATION: D-Arginine

<400> SEQUENCE: 77

Arg Leu Trp Val Trp Trp Val Trp Arg Arg
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 78

Arg Leu Leu Val Trp Trp Val Leu Arg Arg
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 79

Arg Leu Gly Gly Gly Gly Gly Gly Arg Arg
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 80

Trp Val Arg Leu Trp Trp Arg Arg Val Trp
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 81

Arg Leu Val Val Trp Val Val Trp Arg Arg Lys
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 82

Ile Lys Lys Trp Pro Trp Trp Pro Trp Arg Arg Lys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 83

Ile Leu Lys Lys Pro Trp Trp Pro Trp Arg Arg Lys
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 84

Ile Leu Lys Lys Trp Trp Trp Pro Trp Arg Arg Lys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 85

Ile Leu Lys Lys Trp Pro Trp Trp Trp Arg Arg Lys
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 86

Ile Leu Lys Lys Trp Pro Trp Trp Pro Arg Arg Lys
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 87

Ile Leu Lys Lys Trp Pro Trp Trp Pro Trp Arg Arg
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 88

Ile Leu Lys Lys Trp Pro Trp Trp Pro Trp Lys

```
<210> SEQ ID NO 89
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 89

Ile Leu Lys Lys Trp Pro Trp Trp Pro Trp Arg
 1               5                  10

<210> SEQ ID NO 90
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 90

Leu Trp Pro Trp Trp Pro Trp Arg Arg Lys
 1               5                  10

<210> SEQ ID NO 91
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 91

Leu Arg Trp Trp Trp Pro Trp Arg Arg Lys
 1               5                  10

<210> SEQ ID NO 92
<211> LENGTH: 8
<212> TYPE: PRT
<213> ORGANISM: Artificial Sequence
<220> FEATURE:
<223> OTHER INFORMATION: Indolicidin peptide analogs

<400> SEQUENCE: 92

Leu Arg Trp Pro Trp Trp Pro Trp
 1               5

<210> SEQ ID NO 93
<211> LENGTH: 9
<212> TYPE: PRT
<213> ORGANISM: Artificial Sequence
<220> FEATURE:
<223> OTHER INFORMATION: Indolicidin peptide analogs

<400> SEQUENCE: 93

Trp Pro Trp Trp Pro Trp Arg Arg Lys
 1               5

<210> SEQ ID NO 94
<211> LENGTH: 9
<212> TYPE: PRT
<213> ORGANISM: Artificial Sequence
<220> FEATURE:
<223> OTHER INFORMATION: Indolicidin peptide analogs

<400> SEQUENCE: 94

Arg Trp Trp Trp Pro Trp Arg Arg Lys
 1               5
```

```
<210> SEQ ID NO 95
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 95

Ala Leu Arg Trp Pro Trp Trp Pro Trp Arg Arg Lys
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 96

Ile Ala Arg Trp Pro Trp Trp Pro Trp Arg Arg Lys
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 97

Ile Leu Ala Trp Pro Trp Trp Pro Trp Arg Arg Lys
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 98

Ile Leu Arg Ala Pro Trp Trp Pro Trp Arg Arg Lys
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 99

Ile Leu Arg Trp Ala Trp Trp Pro Trp Arg Arg Lys
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 100

Ile Leu Arg Trp Pro Ala Trp Pro Trp Arg Arg Lys
1               5                   10
```

<210> SEQ ID NO 101
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 101

Ile Leu Arg Trp Pro Trp Ala Pro Trp Arg Arg Lys
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 102

Ile Leu Arg Trp Pro Trp Trp Ala Trp Arg Arg Lys
 1               5                  10

<210> SEQ ID NO 103
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 103

Ile Leu Arg Trp Pro Trp Trp Pro Ala Arg Arg Lys
 1               5                  10

<210> SEQ ID NO 104
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 104

Ile Leu Arg Trp Pro Trp Trp Pro Trp Ala Arg Lys
 1               5                  10

<210> SEQ ID NO 105
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 105

Ile Leu Arg Trp Pro Trp Trp Pro Trp Arg Ala Lys
 1               5                  10

<210> SEQ ID NO 106
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 106

Ile Leu Arg Trp Pro Trp Trp Pro Trp Arg Arg Ala
 1               5                  10

<210> SEQ ID NO 107
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 107

Arg Arg Ile Trp Lys Pro Lys Trp Arg Leu Pro Lys Arg
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 108

Trp Arg Trp Trp Lys Pro Lys Trp Arg Trp Pro Lys Trp
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 109

Trp Arg Trp Trp Lys Pro Lys Trp Arg Trp Pro Lys Trp
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 110

Trp Arg Trp Trp Lys Val Ala Trp Arg Trp Val Lys Trp
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 111

Tyr Arg Tyr Tyr Lys Pro Lys Tyr Arg Tyr Pro Lys Tyr
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 112

Phe Arg Phe Phe Lys Pro Lys Phe Arg Phe Pro Lys Phe
1               5                   10

<210> SEQ ID NO 113

```
<211> LENGTH: 12
<212> TYPE: PRT
<213> ORGANISM: Artificial Sequence
<220> FEATURE:
<223> OTHER INFORMATION: Indolicidin peptide analogs

<400> SEQUENCE: 113

Trp Arg Trp Trp Lys Val Trp Arg Trp Val Lys Trp
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 114

Trp Arg Trp Trp Lys Val Val Trp Arg Trp Val Lys Trp
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 115

Trp Arg Leu Leu Lys Leu Ala Leu Arg Leu Leu Lys Trp
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Indolicidin peptide analogs

<400> SEQUENCE: 116

Leu Arg Phe Leu Lys Trp Ala Phe Arg Leu Trp Lys Leu
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Orn
<220> FEATURE:
<221> NAME/KEY: MOD_RES
<222> LOCATION: (9)...(9)
<223> OTHER INFORMATION: Orn
<220> FEATURE:
<221> NAME/KEY: MOD_RES
<222> LOCATION: (12)...(12)
<223> OTHER INFORMATION: Orn

<400> SEQUENCE: 117

Trp Xaa Trp Trp Xaa Val Ala Trp Xaa Trp Val Xaa Trp
1               5                   10
```

<210> SEQ ID NO 118
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Orn
<220> FEATURE:
<221> NAME/KEY: MOD_RES
<222> LOCATION: (7)...(7)
<223> OTHER INFORMATION: Orn
<220> FEATURE:
<221> NAME/KEY: MOD_RES
<222> LOCATION: (9)...(9)
<223> OTHER INFORMATION: Orn
<220> FEATURE:
<221> NAME/KEY: MOD_RES
<222> LOCATION: (12)...(12)
<223> OTHER INFORMATION: Orn

<400> SEQUENCE: 118

Trp Xaa Trp Trp Xaa Pro Xaa Trp Xaa Trp Pro Xaa Trp
 1               5                  10

<210> SEQ ID NO 119
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (2)...(2)
<223> OTHER INFORMATION: Dbu
<220> FEATURE:
<221> NAME/KEY: MOD_RES
<222> LOCATION: (5)...(5)
<223> OTHER INFORMATION: Dbu
<220> FEATURE:
<221> NAME/KEY: MOD_RES
<222> LOCATION: (7)...(7)
<223> OTHER INFORMATION: Dbu
<220> FEATURE:
<221> NAME/KEY: MOD_RES
<222> LOCATION: (9)...(9)
<223> OTHER INFORMATION: Dbu
<220> FEATURE:
<221> NAME/KEY: MOD_RES
<222> LOCATION: (12)...(12)
<223> OTHER INFORMATION: Dbu

<400> SEQUENCE: 119

Trp Xaa Trp Trp Xaa Pro Xaa Trp Xaa Trp Pro Xaa Trp
 1               5                  10

<210> SEQ ID NO 120
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (3)...(3)
<223> OTHER INFORMATION: Orn
<220> FEATURE:
<221> NAME/KEY: MOD_RES

```
<222> LOCATION: (6)...(6)
<223> OTHER INFORMATION: Orn
<220> FEATURE:
<221> NAME/KEY: MOD_RES
<222> LOCATION: (10)...(10)
<223> OTHER INFORMATION: Orn
<220> FEATURE:
<221> NAME/KEY: MOD_RES
<222> LOCATION: (13)...(13)
<223> OTHER INFORMATION: Orn

<400> SEQUENCE: 120

Leu Xaa Phe Leu Xaa Trp Ala Phe Xaa Leu Trp Xaa Leu
 1               5                  10

<210> SEQ ID NO 121
<211> LENGTH: 14
<212> TYPE: PRT
<213> ORGANISM: Artificial Sequence
<220> FEATURE:
<223> OTHER INFORMATION: Indolicidin peptide analogs

<400> SEQUENCE: 121

Gly Trp Arg Phe Leu Lys Leu Ala Trp Arg Phe Leu Lys Leu
 1               5                  10

<210> SEQ ID NO 122
<211> LENGTH: 13
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (8)...(8)
<223> OTHER INFORMATION: Xaa = Aminoisobutyric acid

<400> SEQUENCE: 122

Leu Arg Phe Leu Lys Trp Xaa Trp Arg Phe Leu Lys Leu
 1               5                  10

<210> SEQ ID NO 123
<211> LENGTH: 11
<212> TYPE: PRT
<213> ORGANISM: Artificial Sequence
<220> FEATURE:
<223> OTHER INFORMATION: Indolicidin peptide analogs

<400> SEQUENCE: 123

Arg Ile Leu Arg Trp Val Trp Arg Ile Leu Arg
 1               5                  10

<210> SEQ ID NO 124
<211> LENGTH: 10
<212> TYPE: PRT
<213> ORGANISM: Artificial Sequence
<220> FEATURE:
<223> OTHER INFORMATION: Indolicidin peptide analogs

<400> SEQUENCE: 124

Ile Leu Arg Trp Val Trp Arg Ile Leu Arg
 1               5                  10

<210> SEQ ID NO 125
<211> LENGTH: 16
<212> TYPE: PRT
<213> ORGANISM: Artificial Sequence
<220> FEATURE:
<223> OTHER INFORMATION: Indolicidin peptide analogs
```

<400> SEQUENCE: 125

Gly Trp Arg Phe Leu Lys Leu Ala Trp Arg Phe Leu Lys Leu Arg Arg
1               5                   10                  15

<210> SEQ ID NO 126
<211> LENGTH: 9
<212> TYPE: PRT
<213> ORGANISM: Artificial Sequence
<220> FEATURE:
<223> OTHER INFORMATION: Indolicidin peptide analogs

<400> SEQUENCE: 126

Ile Leu Arg Trp Val Trp Arg Ile Leu
1               5

<210> SEQ ID NO 127
<211> LENGTH: 11
<212> TYPE: PRT
<213> ORGANISM: Artificial Sequence
<220> FEATURE:
<223> OTHER INFORMATION: Indolicidin peptide analogs
<220> FEATURE:
<221> NAME/KEY: MOD_RES
<222> LOCATION: (7)...(7)
<223> OTHER INFORMATION: Xaa = aminoisobutyric acid

<400> SEQUENCE: 127

Arg Ile Leu Arg Trp Xaa Trp Arg Ile Leu Arg
1               5                   10

<210> SEQ ID NO 128
<211> LENGTH: 24
<212> TYPE: PRT
<213> ORGANISM: Artificial Sequence
<220> FEATURE:
<223> OTHER INFORMATION: Indolicidin peptide analogs

<400> SEQUENCE: 128

Lys Lys Trp Trp Arg Arg Val Leu Ser Gly Leu Lys Thr Ala Gly Pro
1               5                   10                  15

Ala Ile Gln Ser Val Leu Asn Lys
            20

<210> SEQ ID NO 129
<211> LENGTH: 24
<212> TYPE: PRT
<213> ORGANISM: Artificial Sequence
<220> FEATURE:
<223> OTHER INFORMATION: Indolicidin peptide analogs

<400> SEQUENCE: 129

Lys Lys Trp Trp Arg Arg Ala Leu Gln Gly Leu Lys Thr Ala Gly Pro
1               5                   10                  15

Ala Ile Gln Ser Val Leu Asn Lys
            20

<210> SEQ ID NO 130
<211> LENGTH: 20
<212> TYPE: PRT
<213> ORGANISM: Artificial Sequence
<220> FEATURE:
<223> OTHER INFORMATION: Indolicidin peptide analogs

<400> SEQUENCE: 130

Lys Lys Trp Trp Arg Arg Val Leu Lys Gly Leu Ser Ser Gly Pro Ala

```
                1               5                   10                  15

Leu Ser Asn Val
            20

<210> SEQ ID NO 131
<211> LENGTH: 20
<212> TYPE: PRT
<213> ORGANISM: Artificial Sequence
<220> FEATURE:
<223> OTHER INFORMATION: Indolicidin peptide analogs

<400> SEQUENCE: 131

Lys Lys Trp Trp Arg Arg Ala Leu Gln Ala Leu Lys Asn Gly Leu Pro
1               5                   10                  15

Ala Leu Ile Ser
            20

<210> SEQ ID NO 132
<211> LENGTH: 26
<212> TYPE: PRT
<213> ORGANISM: Artificial Sequence
<220> FEATURE:
<223> OTHER INFORMATION: Indolicidin peptide analogs

<400> SEQUENCE: 132

Lys Trp Lys Ser Phe Ile Lys Lys Leu Thr Ser Ala Ala Lys Lys Val
1               5                   10                  15

Val Thr Thr Ala Lys Pro Leu Ile Ser Ser
            20                  25

<210> SEQ ID NO 133
<211> LENGTH: 26
<212> TYPE: PRT
<213> ORGANISM: Artificial Sequence
<220> FEATURE:
<223> OTHER INFORMATION: Indolicidin peptide analogs

<400> SEQUENCE: 133

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 134
<211> LENGTH: 28
<212> TYPE: PRT
<213> ORGANISM: Artificial Sequence
<220> FEATURE:
<223> OTHER INFORMATION: Indolicidin peptide analogs

<400> SEQUENCE: 134

Lys Trp Lys Leu Phe Lys Lys Ile Gly Ile Gly Ala Val Leu Lys Val
1               5                   10                  15

Leu Thr Thr Gly Leu Pro Ala Leu Lys Leu Thr Lys
            20                  25

<210> SEQ ID NO 135
<211> LENGTH: 26
<212> TYPE: PRT
<213> ORGANISM: Artificial Sequence
```

```
<220> FEATURE:
<223> OTHER INFORMATION: Indolicidin peptide analogs

<400> SEQUENCE: 135

Lys Trp Lys Ser Phe Ile Lys Lys Leu Thr Thr Ala Val Lys Val
 1               5                  10                  15

Leu Thr Thr Gly Leu Pro Ala Leu Ile Ser
            20                  25

<210> SEQ ID NO 136
<211> LENGTH: 26
<212> TYPE: PRT
<213> ORGANISM: Artificial Sequence
<220> FEATURE:
<223> OTHER INFORMATION: Indolicidin peptide analogs

<400> SEQUENCE: 136

Lys Trp Lys Ser Phe Ile Lys Asn Leu Thr Lys Val Leu Lys Val
 1               5                  10                  15

Val Thr Thr Ala Leu Pro Ala Leu Ile Ser
            20                  25

<210> SEQ ID NO 137
<211> LENGTH: 26
<212> TYPE: PRT
<213> ORGANISM: Artificial Sequence
<220> FEATURE:
<223> OTHER INFORMATION: Indolicidin peptide analogs

<400> SEQUENCE: 137

Lys Trp Lys Ser Phe Ile Lys Lys Leu Thr Ser Ala Ala Lys Val
 1               5                  10                  15

Leu Thr Thr Gly Leu Pro Ala Leu Ile Ser
            20                  25

<210> SEQ ID NO 138
<211> LENGTH: 26
<212> TYPE: PRT
<213> ORGANISM: Artificial Sequence
<220> FEATURE:
<223> OTHER INFORMATION: Indolicidin peptide analogs

<400> SEQUENCE: 138

Lys Trp Lys Leu Phe Ile Lys Lys Leu Thr Pro Ala Val Lys Val
 1               5                  10                  15

Leu Leu Thr Gly Leu Pro Ala Leu Ile Ser
            20                  25

<210> SEQ ID NO 139
<211> LENGTH: 18
<212> TYPE: PRT
<213> ORGANISM: Artificial Sequence
<220> FEATURE:
<223> OTHER INFORMATION: Indolicidin peptide analogs

<400> SEQUENCE: 139

Gly Lys Pro Arg Pro Tyr Ser Pro Ile Pro Thr Ser Pro Arg Pro Ile
 1               5                  10                  15

Arg Tyr

<210> SEQ ID NO 140
<211> LENGTH: 12
<212> TYPE: PRT
<213> ORGANISM: Artificial Sequence
```

```
<220> FEATURE:
<223> OTHER INFORMATION: Indolicidin peptide analogs

<400> SEQUENCE: 140

Arg Leu Ala Arg Ile Val Val Ile Arg Val Ala Arg
1               5                   10
```

ANTIMICROBIAL AND ANTI-INFLAMMATORY PEPTIDES

CROSS-REFERENCE TO RELATED APPLICATIONS

This application is a division of U.S. patent application Ser. No. 10/229,368, filed Aug. 26, 2002 (allowed), which claims the benefit of U.S. Provisional Patent Application No. 60/315,003, filed Aug. 24, 2001, which applications are incorporated herein by reference in their entireties.

TECHNICAL FIELD

The present invention relates generally to the treatment of inflammatory disease and/or infectious disease and, more specifically, to compositions comprising peptides (e.g., cationic peptides) having antimicrobial and/or anti-inflammatory activity and therapeutic uses thereof.

BACKGROUND OF THE INVENTION

Inflammation is a component of the pathogenesis of a number of human diseases, as well as a result of physical, chemical or traumatic damage (i.e., inflammation is the response of living tissue to damage). In general, the inflammatory response results in the systemic release of endogenous chemical mediators, which cause vasodilation, emigration of neutrophils, chemotaxis, and increased vascular permeability. The changes that result from an inflammatory response are essentially the same, regardless of the cause and regardless of where the insult arises. The inflammatory responses may be acute (short lived) or chronic (longer lasting).

The development of inflammatory reactions is controlled by cytokines, by products of the plasma enzyme systems (complement, coagulation, kinin, and fibrinolytic pathways), by lipid mediators (prostaglandins and leukotrienes) released from different cells, and by vasoactive mediators released from mast cells, basophils and platelets. Fast-acting mediators, such as vasoactive amines and the products of the kinin system, modulate the immediate response. Later, newly synthesized mediators such as leukotrienes are involved in the accumulation and activation of other cells. Once leukocytes have arrived at a site of inflammation, they release mediators that control the later accumulation and activation of other cells. Thus, the cytokine system is clearly important for homeostatis when cytokine activation is location (i.e., acting nearby as a surface-bound or diffusible form), but when cytokine production is sustained and/or systemic, there is no doubt that cytokines contribute to the signs, symptoms, and pathology of inflammatory, infections, autoimmune, and malignant diseases.

Typically, an inflammatory response is beneficial because the site of inflammation will have increased access to nutrients, oxygen, antibodies and therapeutic drugs, as well as increased fibrin formation, dilution of toxins, and stimulation of an immune response. However, an inflammatory response may have negative consequences, such as tissue damage caused by the release of lysosomal enzymes by inflammatory cells (neutrophils and macrophages) or an inappropriate response may result in a life threatening hypersensitivity reaction (e.g., asthma or anaphylaxis).

Accordingly, such detrimental inflammatory responses (often referred to as inflammatory diseases) are often treated with anti-inflammatory drugs. There are two major types of anti-inflammatory drugs, corticosteroids and non-steroidal anti-inflammatory drugs (NSAIDs). However, a detrimental consequence of therapies with corticosteroids and NSAIDs is an inhibition of neutrophil function and a reduction in pathogen killing, which can be particularly dangerous in, for example, an immunocompromised patient. In another example, many people suffer the symptoms of Cushing's syndrome as a side effect of taking corticosteroids for asthma, rheumatoid arthritis, lupus, or other inflammatory diseases. Similarly, NSAIDs have side effects, such as causing anaphylactoid reactions and causing gastrointestinal toxicity.

Therefore, a need exists for identifying agents having anti-inflammatory activity that are not immunosuppressive and/or cause other undesirable side effects. Furthermore, there is a need for agents having both antimicrobial activity and anti-inflammatory activity for use in treating, preventing, or ameliorating infections diseases where concomitant inflammation is a problem, such as in acne vulgaris. Such agents would be useful in a variety of clinical indications having an inflammatory component. The present invention meets such needs, and further provides other related advantages.

SUMMARY OF THE INVENTION

The present invention provides peptides, in particular indolicidin peptides and analogs or derivatives thereof, and methods for using such peptides in a variety of therapeutic settings, such as in treating, preventing, or ameliorating, for example, local or systemic inflammatory diseases associated with acute inflammation (such as that due to microbial infections or acne) or chronic inflammation (such as chronic inflammatory bowel disease or rheumatoid arthritis).

In one aspect, the present invention provides an indolicidin analogue or derivative thereof of up to 35 amino acids, comprising one of the following sequences: 11B11, 11B24, 11B38, 11D21, 11F11, 11F35, 11F43, 11F46, 11F60, 11F61, 11F65, 11F82, 11F83, 11F110, 11J32, 11J33, 11J37, 11J44, 11J45, 11J67, 11J68, 11J84, 11J97, 11J105, 11J115, 11J131, 11J136, 11J148, or 11J157.

In another aspect there is provided a composition comprising any one of the aforementioned peptides, or a combination thereof, and a pharmaceutically acceptable excipient. In certain embodiments, the composition comprises a viscosity-increasing agent, a solvent, and an indolicidin analogue or derivative thereof of up to 35 amino acids, comprising one of the following sequences: 11B11, 11B24, 11B38, 11D21, 11F11, 11F35, 11F43, 11F46, 11F60, 11F61, 11F65, 11F82, 11F83, 11F110, 11J32, 11J33, 11J37, 11J44, 11J45, 11J67, 11J68, 11J84, 11J97, 11J105, 11J115, 11J131, 11J136, 11J148, or 11J157. In another embodiment, the aforementioned composition further comprises a buffering agent. In still another embodiment, the composition further comprising a buffering agent has a pH ranging from about 3 to about 8. In yet another embodiment the viscosity-increasing agent is dextran, polyvinylpyrrolidone, hydroxyethyl cellulose, or hydroxy-propyl methylcellulose. In another embodiment, the present invention provides a composition comprising a buffering agent, a solvent, and an indolicidin analogue or derivative thereof of up to 33 amino acids, comprising one of the following sequences: 11B11, 11B24, 11B38, 11D21, 11F11, 11F35, 11F43, 11F46, 11F60, 11F61, 11F65, 11F82, 11F83, 11F110, 11J32, 11J33, 11J37, 11J44, 11J45, 11J67, 11J68, 11J84, 11J97, 11J105, 11J115, 11J131, 11J136, 11J148, or 11J157. In related embodiments, the aforementioned composition having a pH ranging from about 3 to about 8.

In other embodiments, any of the aforementioned compositions wherein the solvent is selected from the group consisting of water, glycerin, propylene glycol, isopropanol, ethanol, and methanol. In further embodiments, any of the aforementioned compositions further comprising a preservative. In a further embodiment, any of the aforementioned compositions having a preservative wherein the preservative comprises benzoic acid, benzyl alcohol, phenoxyethanol, methylparaben, propylparaben, or a combination thereof. As used herein, any reference to an acid may include a free acid, a salt, and any ester thereof. In other embodiments, any of the aforementioned compositions further comprise a humectant and a preservative.

In a further aspect there is provided a method treating, preventing, or ameliorating inflammation at a target site, comprising applying to the target site an indolicidin analogue or derivative thereof of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In other embodiments, the invention provides a method for treating, preventing, or ameliorating inflammation at a target site, comprising applying to the target site a composition comprising a viscosity-increasing agent, a solvent, and an indolicidin analogue or derivative thereof of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In yet another embodiment, there is provided a method for treating, preventing, or ameliorating inflammation, comprising administering parenterally a composition comprising a buffering agent, a solvent, and an indolicidin analogue or derivative thereof of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In still another embodiment, provided is a method for treating, preventing, or ameliorating inflammation, comprising administering parenterally a composition comprising a pharmaceutically acceptable diluent and an indolicidin analogue or derivative thereof of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In other embodiments, any of the aforementioned methods wherein the inflammation is acute, adhesive, atrophic catarrhal, chronic, croupous, degenerative, exudative, fibrinopurulent, fibrinous, granulomatous, interstitial, necrotic, proliferative, pseudomembranous, purulent, sclerosing, serofibrinous, serous, or subacute. In further embodiments, any of the aforementioned methods wherein the inflammation at the target site is associated with a condition is acne, arthritis, autoimmune disease, burn, Crohn's disease, colitis, contact hypersensitivity, delayed type hypersensitivity, eczema, endotoxin shock syndrome, fibromyositis, graft rejection, lichen, microbial, infection, multiple sclerosis, parapsoriasis, psoriasis, sclerosis, or seborrhea. In another embodiment any of the aforementioned methods wherein the inflammation is associated with a medical device.

These and other aspects of the present invention will become evident upon reference to the following detailed description and attached drawings. In addition, various references are set forth herein which describe in more detail certain procedures or compositions, and are therefore incorporated by reference in their entirety.

DETAILED DESCRIPTION OF THE INVENTION

Figure 1:
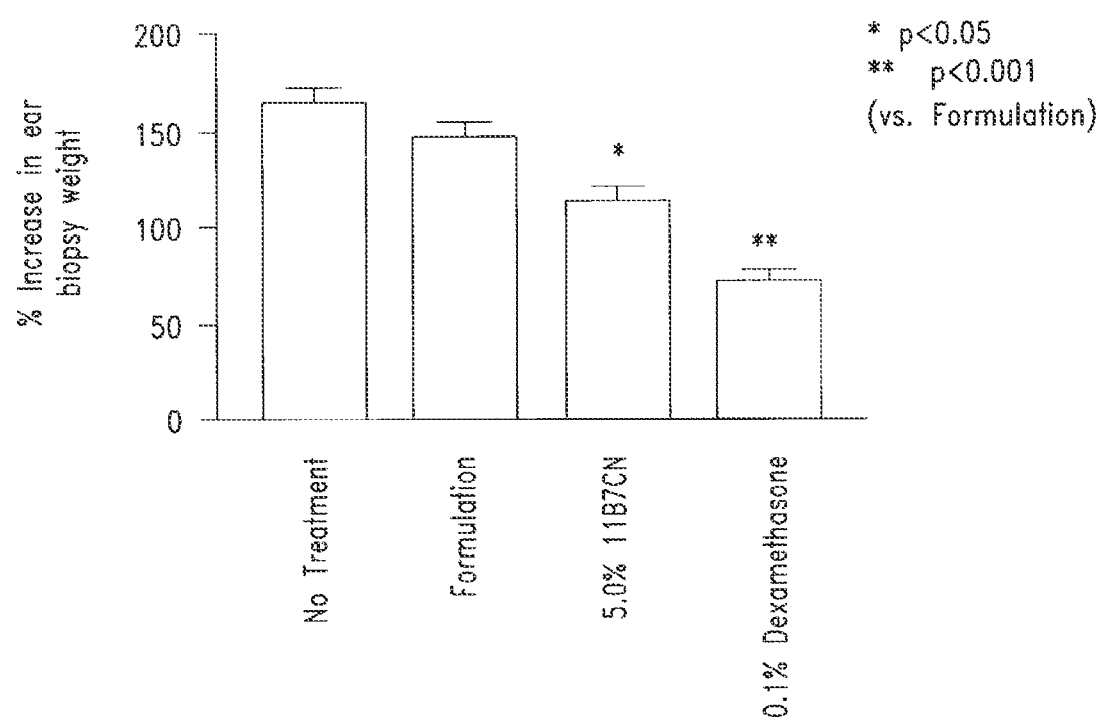
FIG. 1 shows inhibition of chronic inflammation by a 5% indolicidin analog peptide formulation in a murine oxazolone contact delayed-type hypersensitivity model (see also Example 5).
Figure 2:
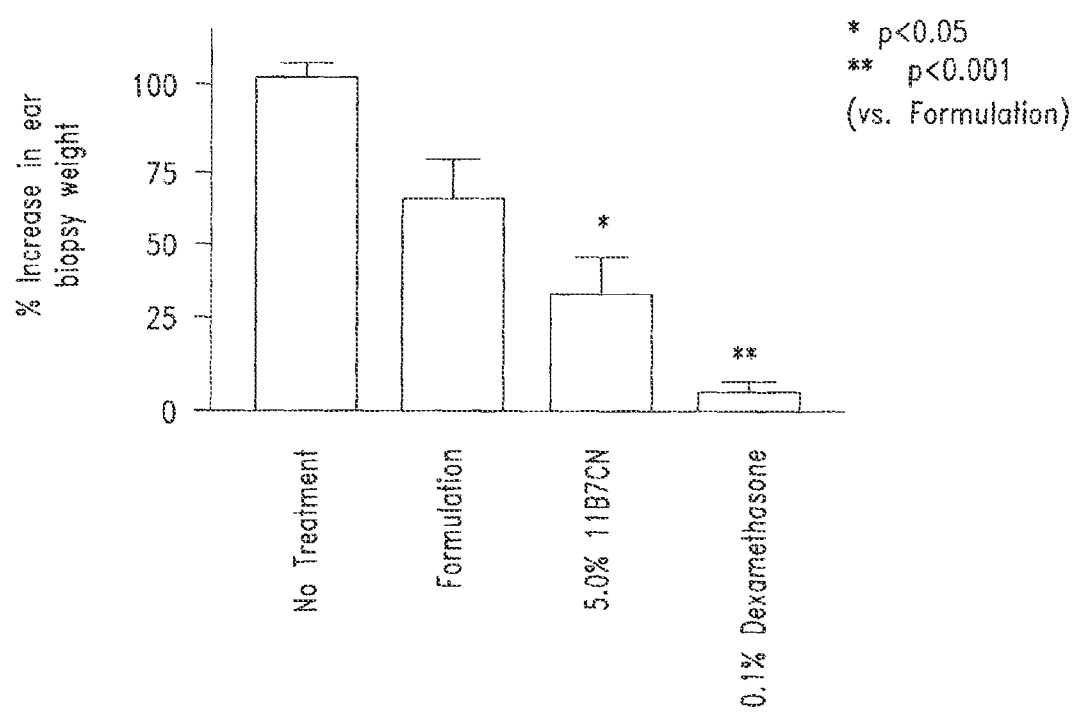
FIG. 2 shows inhibition of acute inflammation by a 5% indolicidin analog peptide formulation in a murine ear edema model TFA (see also Example 6).

As noted above, the present invention provides peptides, and compositions thereof that exhibit antimicrobial and/or anti-inflammatory activity. These peptides can be formulated for use in methods for treating, preventing, and/or ameliorating acute or chronic inflammatory diseases. The invention, therefore, relates generally to the surprising discovery that peptides, particularly but not limited to cationic peptides, may be formulated at a clinically relevant concentration for use as an antimicrobial agent, as an anti-inflammatory agent, and as both an antimicrobial and anti-inflammatory agent. Thus, peptides (e.g., indolicidins and derivatives or analogs thereof) according to the present invention are useful for use in a variety of therapeutic settings, including without limitation, treatment, prevention, or amelioration of inflammatory and infections diseases. Discussed in more detail below are peptides suitable for use within the present invention as well as exemplary therapeutic uses.

Any concentration range recited herein is to be understood to include concentrations of any integer within the range and fractions thereof, such as one tenth and one hundredth of an integer, unless otherwise indicated.

I. Peptides and Analogs or Derivatives Thereof

The present invention is directed generally to peptides having antimicrobial and/or anti-inflammatory activity, which peptides may be produced by a variety of methods (e.g., chemical or recombinant) for use in treating, preventing, or ameliorating inflammatory diseases, as described herein. Suitable antimicrobial and/or anti-inflammatory peptides include, but are not limited to, naturally occurring peptides, which have been isolated, and derivatives or analogs thereof. An "isolated peptide, polypeptide, or protein" is an amino acid sequence that is essentially free from contaminating cellular components, such as carbohydrate, lipid, nucleic acid (DNA or RNA), or other proteinaceous impurities associated with the polypeptide in its natural environment. Preferably, the isolated peptide or polypeptide is sufficiently pure for therapeutic use at a desired dose.

An antimicrobial and/or anti-inflammatory peptide of the present invention may be a recombinant peptide or a synthetic peptide, or a combination thereof. Peptides may be synthesized by standard chemical methods, including synthesis by an automated procedure. In general, peptide analogs are synthesized based on the standard solid-phase Fmoc protection strategy with HATU as the coupling agent. The peptide is cleaved from the solid-phase resin with trifluoroacetic acid containing appropriate scavengers, which also de-protects side chain functional groups. Crude peptide is further purified using preparative reversed-phase chromatography (e.g., RP-HPLC). Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides. Peptides may be synthesized as a linear molecule or as branched molecules. Branched peptides typically contain a core peptide that provides a number of attachment points for additional peptides. Lysine is most commonly used for the core peptide because it has one carboxyl functional group and two (alpha and epsilon) amine functional groups. Other diamine acids can also be used. Preferably, either two or three levels of geometrically branched lysines are used; these cores form a tetrameric and octameric core structure, respectively (Tam, *Proc. Natl. Acad. Sci USA* 85:5409, 1988).

As is known in the art, many antimicrobial peptides are cationic. For example, a cationic peptide is a peptide that typically exhibits a positive charge at neutral pH and contains at least one basic amino acid (e.g., arginine, lysine, histidine). In one preferred embodiment, the antimicrobial and/or anti-inflammatory peptide is a cationic peptide. In addition, a cationic peptide generally comprises an amino acid sequence having 3 molecular mass of about 0.5 kDa (i.e., approximately five amino acids in length) to about 10 kDa (i.e., approximately 100 amino acids in length), or a molecular mass of any integer, or fraction thereof (including a one tenth and one hundredth of an integer), ranging from about 0.5 kDa to about 10 kDa. Preferably, a cationic peptide has a molecular mass ranging from about 0.5 kDa to about 5 kDa (i.e., approximately from about 5 amino acids to about 45 amino acids in length), more preferably from about 1 kDa to about 4 kDa (i.e., approximately from about 10 amino acids to about 35 amino acids in length), and most preferably from about 1 kDa to about 2 kDa (i.e., approximately from about 10 amino acids to about 18 amino acids in length). In another preferred embodiment, the cationic peptide is part of a larger peptide or polypeptide sequence having, for example, a total of up to 100 amino acids, more preferably up to 50 amino acids, even more preferably up to 35 amino acids, and most preferably up to 15 amino acids. The present invention contemplates a cationic peptide having an amino acid sequence of 5 to 100 amino acids, with the number of amino acids making up the peptide sequence comprising any integer in that range. A cationic peptide may exhibit antibacterial activity, anti-endotoxin activity, antifungal activity, antiparasite activity, antiviral activity, anticancer activity, anti-inflammatory activity, wound healing activity, and synergistic activity with other peptides or antimicrobial compounds, or a combination thereof.

Exemplary cationic peptides include, without limitation, cecropins, normally made by lepidoptera (Steiner et al., *Nature* 292:246, 1981) and diptera (Merrifield et al., *Ciba Found. Symp.* 186:5, 1994), by porcine intestine (Lee et al., *Proc. Nat'l. Acad. Sci. USA* 86:9159, 1989), and by blood cells of a marine protochordate (Zhao et al., *FEBS Lett.* 412:144, 1997); synthetic analogs of cecropin A, melittin, and cecropin-melittin chimeric peptides (Wade et al., *Int. J. Pept. Protein Res.* 40:429, 1992); cecropin B analogs (Jaynes et al., *Plant Sci.* 89:43, 1993); chimeric cecropin A/B hybrids (Düring, *Mol. Breed.* 2:297, 1996); magainins (Zasloff, *Proc. Nat'l Acad. Sci USA* 84:5449, 1987); cathelin-associated antimicrobial peptides from leukocytes of humans, cattle, pigs, mice, rabbits, and sheep (Zanetti et al., *FEBS Lett.* 374:1, 1995); vertebrate defensins, such as human neutrophil defensins [HNP 1-4]; Paneth cell defensins of mouse and human small intestine (Oulette and Selsted, *FASEB J.* 10:1280, 1996; Porter et al., *Infect. Immun.* 65:2396, 1997); vertebrate β-defensins, such as HBD-1 of human epithelial cells (Zhao et al., *FEBS Lett.* 368:331, 1995); HBD-2 of inflamed human skin (Harder et al., *Nature* 387:861, 1997); bovine β-defensins (Russell et al., *Infect. Immun.* 64:1565, 1996); plant defensins, such as Rs-AFP1 of radish seeds (Fehlbaum et al., *J. Biol. Chem.* 269:33159, 1994); α- and β-thionins (Stuart et al., *Cereal Chem.* 19:288, 1942; Bohlmann and Apel, *Annu. Rev. Physiol. Plant Mol. Biol.* 42:227, 1991); γ-thionins (Broekaert et al., *Plant Physiol.* 108:1353, 1995); the anti-fungal drosomycin (Fehlhaum et al., *J. Biol. Chem.* 269:33159, 1994); apidaecins, produced by honey bee, bumble bee, cicada killer, hornet, yellow jacket, and wasp (Casteels et al., *J. Biol. Chem.,* 269:26107, 1994; Levashina et al., *Eur. J. Biochem* 233:694, 1995); cathelicidins, such as indolicidin and derivatives or analogs thereof from bovine neutrophils (Falla et al., *J. Biol. Chem.* 277:19298, 1996); bacteriocins, such as nisin (Delves-Broughton et al., Antonie van Leeuwenhoek *J. Microbial.* 69:193, 1996); and the protegrins and tachyplesins, which have antifungal, antibacterial, and antiviral activities (Tumamura et al., *Biochim. Biophys. Acta* 1163:209, 1993; Aumelas et al., *Eur. J. Biochem.* 237:515, 1996; Iwanga et al., *Ciba Found. Symp.* 186:160, 1994).

In certain embodiments, preferred cationic peptides of the present invention are indolicins or analogs or derivatives thereof (see Table 1 of Example 1). Natural indolicidins may be isolated from a variety of organisms. For example, indolicidin isolated from bovine neutrophils is a 13 amino acid peptide that is tryptophan-rich and amidated at the C-terminus (see Selsted et al., *J. Biol. Chem.* 267:4292, 1992). As noted above, a preferred indolicidin or analog or derivative thereof comprises 5 to 45 amino acids, more preferably 7 to 35 amino acids, even more preferably 8 to 25 amino acids, and most preferably 10 to 14 amino acids (see, e.g., Table 1). In certain embodiments, the indolicidin analog or derivative may comprise a peptide having a negative charge (e.g., 1B11) or a neutral or hydrophobic peptide (e.g., 11B24 and 11B38). The indolicidins or analogs or derivatives thereof of the present invention may be used at a concentration ranging from about 0.01% to about 10%, preferably from about 0.5% to about 5%, and more preferably from either about 1% to about 3% or about 4% to about 6%, depending on the intended use and formulation ingredients (where "about" is ±10% of the indicated value). In certain embodiments, the peptide is an indolicidin or an analog or derivative thereof. In preferred embodiments, the indolicidin or analog or derivative thereof is a peptide of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157, which may be used individually or in a cocktail mixture in any one of the compositions described herein or those compositions known in the art.

A peptide of the present invention may be an analog or derivative thereof. As used herein, the terms "derivative" and "analog," when referring to a peptide, polypeptide, or fusion protein, refer to any peptide, polypeptide, or fusion protein that retain essentially the same (at least 50%, and preferably greater than 70, 80, or 90%) or enhanced biological function or activity as such natural peptide, as noted above. In addition, a cationic peptide analogue or derivative is to be understood to include those that no longer have a positive charge (i.e., may be negatively charged, neutral, or hydrophobic) but retain function as noted above. The biological function or activity of such analogs and derivatives can be determined using standard methods (e.g., antimicrobial, anti-inflammatory, DNA and/or protein synthesis inhibitor), such as with the assays described herein. For example, an analog or derivative may be a preproprotein or proprotein, which may be activated by cleavage to produce an active antimicrobial and/or anti-inflammatory peptide. Alternatively, an antimicrobial and/or anti-inflammatory peptide analog or derivative thereof can be identified by the ability to specifically bind to or associate with anti-peptide antibodies.

An antimicrobial and/or anti-inflammatory peptide analog or derivative may have, for example, one or more deletion, insertion, or modification of any amino acid residue, including the N- or C-terminal amino acids. Within the scope of this invention are modified an antimicrobial and/or anti-inflammatory peptides, such as, for example, peptides having an acetylated, acylated, acryloylated, alkylated, glycosylated (e.g., glucosylated), PEGylated, myristylated, and the like N-terminal amino acid modification; having an esterified, amidated, homoserine/homoserine lactone, caprolactam and the like C-terminal amino acid modification; or having a polyalkylene glycol (e.g., polyethylene glycol) conjugated to any free amino group. A preferred modification of the C-terminal amino acid is homoserine/homoserine lactone and more preferably is amidation. Therefore, as used herein, a peptide having a particular sequence will be understood to encompass not only the natural peptide, but also modified forms thereof. For example, when referring to peptide "11B7," this includes the natural peptide (11B7-OH), the N-terminal acetylated 11B7 peptide (A-11B7), N-terminal acryloylated 11B7 peptide (Nt-acryloyl-11B7), N-terminal glucosylated 11B7 peptide (Nt-glucosyl-11B7), the carboxy terminal homoserine/homoserine lactone 11B7 (11B7H or 11B7HS), the carboxy terminal amidated 11B7 (11B7CN), and the like.

A peptide analog or derivative may also be part of a fusion protein. Fusion proteins, or chimeras, include fusions of one or more antimicrobial and/or anti-inflammatory peptides, and fusions of antimicrobial and/or anti-inflammatory peptides with non-antimicrobial and/or anti-inflammatory peptides or polypeptides. Additionally, the peptide may be modified to form a polymer-modified peptide. The peptides may also be labeled, such as with a radioactive label, a fluorescent label, a mass spectrometry tag, biotin, and the like, by methods known in the art.

Another example of an analog or derivative includes a antimicrobial and/or anti-inflammatory peptide that has one or more conservative amino acid substitutions, as compared with the amino acid sequence of a naturally occurring peptide. Among the common amino acids, a "conservative amino acid substitution" is illustrated, for example, by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine, or a combination thereof. Furthermore, an analog or derivative of a cationic peptide may include, for example, non-protein amino acids, such as precursors of normal amino acids (e.g., homoserine and diaminopimelate), intermediates in catabolic pathways (e.g., pipecolic acid, and D-enantiomers of normal amino acids), and amino acid analogs (e.g., azetidine-2-carboxylic acid and canavanine).

The amino acid designations are herein set forth as either the standard one- or three-letter code. Unless otherwise indicated, a named amino acid refers to the L-enantiomer. Polar amino acids include asparagine (Asp or N) and glutamine (Gln or Q); as well as basic amino acids such as arginine (Arg or R), lysine (Lys or K), histidine (His or H), and derivatives thereof; and acidic amino acids such as aspartic acid (Asp or D) and glutamic acid (Glu or E), and derivatives thereof. Hydrophobic amino acids include tryptophan (Trp or W), phenylalanine (Phe or F), isoleucine (Ile or I), leucine (Leu or L), methionine (Met or M), valine (Val or V), and derivatives thereof; as well as other non-polar amino acids such as glycine (Gly or G), alanine (Ala or A), proline (Pro or P), and derivatives thereof. Amino acids of intermediate polarity include serine (Ser or S), threonine (Thr or T), tyrosine (Tyr or Y), cysteine (Cys or C), and derivatives thereof. A capital letter indicates an L-enantiomer amino acid; a small letter indicates a D-enantiomer amino acid. An antimicrobial and/or anti-inflammatory peptide analog or derivative thereof may include any one or combination of the above-noted alterations to the natural peptide, or any other modification known in the art.

A. Other Antimicrobial and Anti-Inflammatory Agents

The indolicidin and analogs or derivatives thereof of the present invention may be used individually, or may be used in combination with one or more different indolicidin and analog or derivative thereof, with one or more cationic peptides, with one or more conventional antimicrobial agents, or with one or more anti-inflammatory agents known in the art, as described herein. Thus, synergistic combinations of an antimicrobial and/or anti-inflammatory peptide and an antimicrobial agent may permit a reduction in the dosage of one or both agents in order to achieve a similar or improved therapeutic effect. This would allow the use of smaller doses and, therefore, would decrease the potential incidence of toxicity (e.g., from aminoglycosides) and towering costs of expensive antimicrobials (e.g., vancomycin). Concurrent or sequential administration of an antimicrobial and/or anti-inflammatory peptide formulation and an antimicrobial agent and/or anti-inflammatory agent composition is expected to provide more effective treatment of infections, caused by a variety of microorganisms (e.g., bacteria, viruses, fungi, and parasites), and/or inflammatory diseases. In particular, successful treatment, or prevention of infections disease can be achieved by using the antimicrobial and/or anti-inflammatory peptides with antimicrobial agents and/or anti-inflammatory agents at doses below what is normally a therapeutically effective dose-when these antimicrobials and anti-inflammatorys are used individually. Alternatively, an antibiotic agent and/or anti-inflammatory agent with an antimicrobial and/or anti-inflammatory peptide can be administered using a normally effective therapeutic dose for each active component, but wherein the combination of the two or more agents provides even more potent effects.

As noted above, the preferred antimicrobial and/or anti-inflammatory peptides may be used in a synergistic combination with other known antimicrobial agents. Antibacterial agents include, but are not limited to, penicillins, cephalosporins, carbacephems, cephamycins, carbapenems, monobactams, aminoglycosides, glycopeptides, quinolones, tetracyclines, macrolides, and fluoroquinolones. Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Caphalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69172-56-7); Cefprozil (CAS Registry No.: 92665-29-7); Loracarbef (CAS Registry No.: 121961-22-6) Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0) Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79960-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobinate (CAS Registry No.: 3847-29-8); Erythromycin stearate (CAS Registry No.: 643-22-1); Vanomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavunate; combinations of Piperacillin and Tazobactam; and their various salts, acids, bases, and other derivatives, and combinations thereof.

The antimicrobial and/or anti-inflammatory peptide may also be used in combination with anti-fungal agents. Exemplary anti-fungal agents include, but are not limited to, terbinafine hydrochloride, nystatin, amphotericin B, griscofulvin, ketoconazole, miconazole nitrate, flucytosine, fluconazole, itraconazole, clotriamzole, benzoic acid, salicylic acid, and selenium sulfide.

The antimicrobial and/or anti-inflammatory peptide may also be used in combination with anti-viral agents. Exemplary anti-viral agents include, but are not limited to, amantadine hydrochloride, rimantadin, acyclovir, famciclovir, foscarnet, ganciclovir sodium, idoxuridine, ribavirin, sorivudine, trifluoridine, valacyclovir, vidarabin, didanosine, stavudine, zalcitabine, zidovudine, interferon alpha, and edoxudine.

The antimicrobial and/or anti-inflammatory peptide may also be used in combination with anti-parasitic agents. Exemplary anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

As noted above, the preferred antimicrobial and/or anti-inflammatory peptides may be used in a synergistic combination with other known anti-inflammatory agents. Anti-inflammatory agents include, without limitation, oral or inhaled corticosteroids (e.g., hydrocortisone, triamcinolone), non-steroidal anti-inflammatory drugs (NSAIDs), (e.g., nabumetone, indomethicin, naproxen, ibuprofen), anti-inflammatory cytokines (e.g., IL-4, IL-10, IL-13), cytokine antagonists (e.g., IL-1 receptor antagonist, TNF-α monoclonal antibody, soluble TNF receptor, platelet factor 4), and the like. See also, e.g., U.S. Pat. No. 6,190,691; U.S. Pat. No. 5,776,892; U.S. Pat. No. 4,816,449; and U.S. Pat. No. RE37,263.

B. Antibodies

In another aspect, antibodies may be generated to a specific antimicrobial and/or anti-inflammatory peptide and analog or derivative thereof using multiple antigenic peptides (MAPs) that contain approximately eight copies of the peptide linked to a small non-immunogenic peptidyl core to form an immunogen (see, in general, *Antibodies: A Laboratory Manual*, Harlow and Lane (eds.), Cold Spring Harbor Laboratory Press, 1988). Alternatively, the target peptide may be conjugated to bovine serum albumin (BSA), ovalbumin, or another suitable conjugate. For example, the MAP or peptide conjugate may be injected subcutaneously into rabbits or into mice or other rodents, where they may have sufficiently long half-lives to facilitate antibody production. After twelve weeks, blood samples are taken and serum is separated for testing in an ELISA assay against the original peptide, with a positive result indicating the presence of antibodies specific to the target peptide. This serum can then be stored and used in ELISA assays to specifically measure the amount of the specific peptide and/or analog or derivative thereof. Alternatively, other standard methods of antibody production may be employed, such as generation of monoclonal antibodies.

Within the context of the present invention, antibodies are understood to include, inter alia, monoclonal antibodies, polyclonal antibodies, anti-idiotypic antibodies, and antibody fragments (e.g., Fab, and F(ab')$_2$, F$_v$ variable regions, or complementarily determining regions). Antibodies are generally accepted as specific against antimicrobial and/or anti-inflammatory peptides, such as indolicidin and analogs or derivatives thereof, if they bind with a K$_d$ of greater than or equal to $10^{-7}$ M, preferably greater than of equal to $10^{-8}$ M, and more preferably greater than or equal to $10^{-9}$ M. The affinity of a monoclonal antibody or binding partner may be readily determined by one of ordinary skill in the art (see, e.g., Scatchard, *Ann. N.Y. Acad. Sci.* 51:660-672, 1949). Once suitable antibodies have been identified, they may be isolated or purified by many techniques well known to those of ordinary skill in the art.

Monoclonal antibodies may also be readily generated from hybridoma cell lines using conventional techniques (see U.S. Pat. Nos. Re 32,011, 4,902,614, 4,543,439, and 4,411,993; see also *Antibodies: A Laboratory Manual*, 1988). Briefly, within one embodiment, a subject animal, such as a rat or mouse, is injected with a peptide of choice. The peptide is generally administered in an emulsion with an adjuvant, such as Freund's complete or incomplete adjuvant, which is intended to increase the immune response. The animal is generally boosted at least once prior to harvest of the spleen and/or lymph nodes and immortalization of those cells. Various immortalization techniques, such as mediated by Epstein-Barr virus or fusion to produce a hybridoma, may be used. In a preferred embodiment, immortalization occurs by fusion with a suitable myeloma cell line to create a hybridoma that secretes monoclonal antibody. Suitable myeloma lines include, for example, NS-1 (ATCC No. TIB 18), and P3X63-Ag 8.653 (ATCC No. CRL 1580). The preferred fusion partners do not express endogenous antibody-genes. After about seven days, the hybridomas may be screened for the presence of antibodies that are reactive against a particular peptide and analog or derivative thereof. A wide variety of assays may be utilized (see *Antibodies: A Laboratory Manual*, 1988).

Other techniques known in the art may be utilized to construct monoclonal antibodies (see Huse et al., *Science* 346:1275-1281, 1989; Sastry et al., *Proc. Natl. Acad. Sci. USA* 86:5728-5732, 1989; Alting-Mees et al., *Strategies in Molecular Biology* 3:1-9, 1990; describing recombinant techniques). These techniques include cloning heavy and light chain immunoglobulin cDNA in suitable vectors, such as λImmunoZap(H) and λImmunoZap(L). These recombinants may be screened individually or co-expressed to form Fab fragments or antibodies (see Huse et al., supra; Sastry, et al., supra). Positive plaques may subsequently be converted into non-lytic plasmids to allow high-level expression of monoclonal antibody fragments in a host, such as *E. coli*.

Similarly, portions or fragments of antibodies, such as Fab and Fv fragments, may also be constructed utilizing conventional enzymatic digestion or recombinant DNA techniques to yield isolated variable regions of an antibody. Within one embodiment, the genes that encode the variable region from a hybridoma producing a monoclonal antibody of interest are amplified using nucleotide primers for the variable region. In addition, techniques may be utilized to change a "murine" antibody to a "human" antibody, without altering the binding specificity of the antibody to the peptide and analog or derivative thereof.

II. Nucleic Acids Encoding Antimicrobial and/or Anti-Inflammatory Peptides

Nucleic acid molecules encoding antimicrobial and/or anti-inflammatory peptides may be isolated from natural sources, may be obtained by automated synthesis of nucleic acid molecules, or may be obtained by using the polymerase chain reaction (PCR) with oligonucleotide primers having nucleotide sequences that are based upon known nucleotide sequences of antimicrobial and/or anti-inflammatory peptide genes. In the latter approach, a antimicrobial and/or anti-inflammatory peptide gene is synthesized using mutually priming oligonucleotides (see, for example, Ausubel et al. (eds.), *Short Protocols in Molecular Biology*, $3^{rd}$ Edition, pages 8-8 to 8-9, John Wiley & Sons, 1995, hereinafter referred to as "Ausubel (1995)"). Established techniques using the polymerase chain reaction provide the ability to synthesize DNA molecules of at least two kilobases in length (Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in *Methods in Molecular Biology, Vol.* 15: *PCR Protocols: Current Methods and Applications*, White (ed.), pages 263-268, Humana Press, Inc., 1993; Holowachuk et al., *PCR Methods Appl.* 4:299, 1995).

As noted above, the present invention contemplates analogs or derivatives of natural peptides, which analogs or derivatives may be recombinantly produced by the presently described methods. Nucleotide sequences encoding conservative amino acid analogs or derivatives can be obtained, for example, by oligonucleotide-directed mutagenesis, linker-scanning mutagenesis, mutagenesis using the polymerase chain reaction, and the like (see Ausubel, 1995, at page 8-10 through page 8-22; and McPherson (ed.), *Directed Mutagenesis: A Practical Approach*, IRL Press, 1991).

Although one objective in constructing a peptide variant may be to improve its activity. It may also be desirable to alter the amino acid sequence of a naturally occurring peptide to enhance its production in a recombinant host cell. The presence of a particular codon may have an adverse effect on expression in a particular host; therefore, a DNA sequence encoding the desired peptide is optimized for a particular host system, such as prokaryotic or eukaryotic cells. For example, a nucleotide sequence encoding a radish cationic peptide may include a codon that is commonly found in radish, but is rare for *E. coli*. The presence of a rare codon may have an adverse effect on protein levels when the radish cationic peptide is expressed in recombinant *E. coli*. Methods for altering nucleotide sequences to alleviate the codon usage problem are well known to those of skill in the art (see, e.g., Kane, *Curr. Opin. Biotechnol.* 6:494, 1995; Makrides, *Microbiol. Rev.* 60:512, 1996; and Brown (Ed.), *Molecular Biology LabFax*, BIOS Scientific Publishers, Ltd., 1991, which provides a Codon Usage Table at page 245 through page 253).

Peptides may be synthesized by recombinant techniques (see e.g., U.S. Pat. No. 5,593,866) and a variety of host systems are suitable for production of the antimicrobial and/or anti-inflammatory peptides and analogs or derivatives thereof, including bacteria (e.g., *E. coli*), yeast (e.g., *Saccharomyces cerevisiae*), insect (e.g., Sf9), and mammalian cells (e.g., CHO, COS-7). Many expression vectors have been developed and are available for each of these hosts. Generally, vectors that are functional in bacteria are used in this invention. However, at times, it may be preferable to have vectors that are functional in other hosts. Vectors and procedures for cloning and expression in *E. coli* are discussed herein and, for example, in Sambrook et al. (*Molecular Cloning: A laboratory Manual*, Cold Spring Harbor Laboratory Press, Cold Spring Harbor, N.Y., 1987) and in Ausubel et al., 1995.

A DNA sequence encoding a peptide is introduced into an expression vector appropriate for the host. In preferred embodiments, the gene is clonal into a vector to create a fusion protein. In the case of cationic peptides, the fusion partner is chosen to contain an anionic region such that a bacterial host is protected from the toxic effect of the cationic peptide. This protective region effectively neutralizes the antimicrobial effects of the peptide and also may prevent peptide degradation by host proteases. The fusion partner (carrier protein) of the invention may further function to transport the fusion peptide to inclusion bodies, the periplasm, the outer membrane, or the extracellular environment. Carrier proteins suitable in the context of this invention specifically include, but are not limited to, glutathione-S-transferase (GST), protein A from *Staphyloccus aureus*, two synthetic IgG-binding domains (ZZ) of protein A, outer membrane protein F, β-galactosidase (lacZ), and various products of bacteriophage λ and bacteriophage T7. From the teachings provided herein, it is apparent that other proteins may be used as carriers. Furthermore, the entire carrier protein need not be used. Similarly with cationic peptides, the entire carrier protein need not be used as long as a protective anionic region is present. To facilitate isolation of a peptide sequence, amino acids susceptible to chemical cleavage (e.g., CNBr) or enzymatic cleavage (e.g., V8 protease, trypsin) are used to bridge the peptide and fusion partner. For expression in *E. coli*, the fusion partner is preferably a normal intracellular protein that directs expression toward inclusion body formation. In such a case, following cleavage to release the final product, there is no requirement for renaturation of the peptide. In the present invention, the DNA cassette, comprising fusion partner and peptide gene, may be inserted into an expression vector, which can be a plasmid, virus or other vehicle known in the art. Preferably, the expression vector is a plasmid that contains an inducible or constitutive promoter to facilitate the efficient transcription of the inserted DNA sequence in the host. Transformation of the host cell with the recombinant DNA may be carried out by $Ca^{++}$-mediated techniques, by electroporation, or other methods well known to those skilled in the art.

Briefly, a DNA fragment encoding a peptide is derived from an existing cDNA or genomic clone or synthesized. A convenient method is amplification of the gene from a single-stranded template. The template is generally the product of an automated oligonucleotide synthesis. Amplification primers are derived from the 5' and 3' ends of the template and typically incorporate restriction sites chosen with regard to the cloning site of the vector. If necessary, translational initiation and termination codons can be engineered into the primer sequences. The sequence encoding the protein may be codon-optimized for expression in the particular host. Thus, for example, if the analog fusion protein is expressed in bacteria, codons are optimized for bacterial usage. Codon optimization is accomplished by automated synthesis of the entire gene or gene region, ligation of multiple oligonucleotides, mutagenesis of the native sequence, or other techniques known to those in the art.

Within a preferred embodiment, the vector is capable of replication in bacterial cells. Thus, the vector may contain a bacterial origin of replication. Preferred bacterial origins of replication include f1-ori and col E1 ori, especially the ori derived from pUC plasmids. Low copy number vectors (e.g., pPD100) stray also be used, especially when the product is deleterious to the host. The plasmids also preferably include at least one selectable marker that is functional in the host. A selectable marker gene confers a phenotype on the host that allows transformed cells to be identified and/or selectively grown. Suitable selectable marker genes for bacterial hosts include the chloramphenicol resistance gene ($Cm^r$), ampicillin resistance gene ($Amp^r$), tetracycline resistance gene ($Tc^r$) kanamycin resistance gene ($Kan^r$), and others known in the art. To function in selection, some markers may require a complementary deficiency in the host. The vector may also contain a gene coding for a repressor protein, which is capable of repressing the transcription of a promoter that contains a repressor binding site. Altering the physiological conditions of the cell can depress the promoter. For example, a molecule may be added that competitively binds the repressor, or the temperature of the growth media may be altered. Repressor proteins include, but are not limited to the *E. coli* lacI repressor (responsive to induction by IPTG), the temperature sensitive λcI857 repressor, and the like.

At minimum, the expression vector should contain an expression control sequence, such as a promoter sequence. Other regulatory sequences may also be included. Such sequences may include at least one of an enhancer, a ribosome binding site, a transcription termination signal sequence, a secretion signal sequence, an origin of replication, a selectable marker, and the like, and combinations thereof. The regulatory sequences are operably linked with one another to allow transcription and subsequent translation. In preferred aspects, the plasmids used herein for expression include a promoter designed for expression of the proteins in bacteria. Suitable promoters, including both constitutive and inducible promoters, are widely available and are well known in the art. Commonly used promoters for expression in bacteria include promoters from T7, T3, T5, and SP6 phages, and the trp, lpp, and lac operons. Hybrid promoters (see, U.S. Pat. No. 4,551,433), such as lac and trc, may also be used. Examples of plasmids for expression in bacterial include the pET expression vectors pET3a, pET 11a, pET 12a-c, and pET 15b (see U.S. Pat. No. 4,952,496; available from Novagen, Madison, Wis.). Low copy number vectors e.g., pPD100) can be used for efficient overproduction of peptides deleterious to the *E. coli* host (Dersch et al., *FEMS Microbiol. Lett.* 123: 19, 1994). Bacterial hosts for the T7 expression vectors may contain chromosomal copies of DNA encoding T7 RNA polymerase operably linked to an inducible promoter (e.g., lacUV promoter; see, U.S. Pat. No. 4,952,496), such as found in the *E. coli* strains HMS174 (DE3)pLysS, BL21(DE3)pLysS, HMS174(DE3) and BL21 (DE3). T7 RNA polymerase can also be present on plasmids compatible with the T7 expression vector. The polymerase may be under control of a lambda promoter and repressor (e.g., pGP1-2; Tabor and Richardson, *Proc. Natl. Acad. Sci. USA* 82: 1074, 1985).

In some aspects, the sequence of nucleotides encoding the peptide also encodes a secretion signal, such that the resulting peptide is synthesized as a precursor protein (i.e., proprotein), which is subsequently processed and secreted. The resulting secreted peptide or fusion protein may be recovered from the periplasmic space or the fermentation medium. Sequences of secretion signals suitable for use are widely available and are well known (von Heijne, *J. Mol. Biol.* 184:99-105, 1985).

The peptide product is isolated by standard techniques, such as affinity, size exclusion, or ionic exchange chromatography, HPLC and the like. An isolated peptide should preferably show a major band by Coomassie blue stain of SDS-PAGE, which is preferably at least 75%, 80%, 90%, or 95% of the purified peptide, polypeptide, or fusion protein.

III. Testing Antimicrobial and/or Anti-Inflammatory Peptide and Analogs or Derivatives Thereof Antimicrobial and/or anti-inflammatory peptides, and analogs or derivatives thereof, of the present invention are assessed, either alone or in combination with an antimicrobial agent or another analog, for their potential as antibiotic therapeutic agents using a series of assays. Preferably, all peptides are initially assessed in vitro, the most promising candidates are selected for further assessment in vivo, and then candidates are selected for pre-clinical studies. The in vitro assays include measurement of antibiotic activity, toxicity, solubility, pharmacology, secondary structure, liposome permeabilization and the like. In vivo assays include assessment of efficacy in animal models, antigenicity, toxicity, and the like. In general, in vitro assays are initially performed, followed by in vivo assays.

Generally, peptides are initially tested for (1) antimicrobial activity in vitro; (2) in vitro toxicity to normal mammalian cells; and (3) in vivo toxicity in an animal mode. The peptides that have some antimicrobial activity are preferred, although such activity may not be necessary for enhancing the activity of an antibiotic agent. Also, for in vivo use, peptides should preferably demonstrate acceptable toxicity profiles, as measured by standard procedures, where lower toxicity is preferred. Additional assays may be performed to demonstrate that the peptide is not immunogenic and to examine antimicrobial activity in vivo.

A. In Vitro Assays

Antimicrobial and/or anti-inflammatory peptides, including indolicidin analogs, are assayed by, for example, an agarose dilation MIC assay, a broth dilution, time-kill assay, or equivalent methods. Antimicrobial activity is measured as inhibition of growth or killing of a microorganism (e.g., bacteria, fungi).

Briefly, a candidate antimicrobial and/or anti-inflammatory peptide in Mueller Hinton broth supplemented with calcium and magnesium is mixed with molten agarose. Other broths and agars may be used as long as the peptide can freely diffuse through the medium. The agarose is poured into petri dishes or wells, allowed to solidify, and a test strain is applied to the agarose plate. The test strain is chosen, in part, on the intended application of the peptide. Thus, by way of example, if an indolicidin or analog or derivative thereof with activity against *S. aureus* is desired, a *S. aureus* strain is used. It may be desirable to assay the candidate peptide on several strains and/or on clinical isolates of the test species. Plates are incubated overnight and inspected visually for bacterial growth. A minimum inhibitory concentration (MIC) of a peptide is the lowest concentration of peptide that completely inhibits growth of the organism. Peptides that exhibit good activity against the test strain, or group of strains, typically having an MIC of less than or equal to 16 µg/ml are selected for further testing. Preferred antimicrobial and/or anti-inflammatory peptides or analogs or derivatives thereof may be microbicidal or microbistatic.

Alternatively, time kill curves can be used to determine the difference in growth (e.g., bacterial colony counts) over a set time period, typically 24 hours. Briefly, a suspension of organisms at a known concentration is prepared and a candidate peptide is added. Aliquots of the suspension are removed at set times, diluted, plated on medium, incubated, and counted. MIC is measured as the lowest concentration of peptide that completely inhibits growth of the organism and, in general, lower MIC values are preferred.

Solubility of the peptide in a solvent, broth, or co-solvent, system as described herein is an additional parameter that may be examined. Several different assays may be used, such as appearance in buffer. Briefly, a candidate antimicrobial and/or anti-inflammatory peptide or analog or derivative thereof may be contacted with a solvent, broth, of co-solvent system, and the appearance evaluated according to a scale that ranges from (a) clear, no precipitate, (b) light, diffuse precipitate, to (c) cloudy, heavy precipitate. In general, less precipitate is more desirable, but some precipitate may be acceptable. To assess the level of solubility, for example, a person having ordinary skill in the art may inspect the combination visually, or a variety of spectrophotometric techniques may be used, such as by U.V. or visible light absorbance at the appropriate wavelength.

Additional in vitro assays may be carried out to assess the potential of a candidate peptide or analog or derivative thereof as a therapeutic agent. Such assays include peptide solubility in formulations, pharmacology and stability in blood or plasma, serum protein binding, analysis of secondary structure (e.g., by circular dichroism), liposome permeabilization, and bacterial membrane permeabilization. In general, a pretested embodiment includes a candidate peptide analog or derivative thereof that is soluble, is active in biological fluids, is stable, and has generally equal or greater antimicrobial activity than the natural peptide (e.g., indolicidin).

B. In Vivo Assays

Peptides and analogs or derivative thereof, selected on the basis of the results from the in vitro assays can be further tested in vivo for efficacy, stability, and the like. A variety of methods and animal models are available to assess the antimicrobial activity of selected candidate peptides and analogs or derivative thereof in vivo for their ability to ameliorate microbial infections. Within these assays, a peptide is useful as a therapeutic if inhibition of microbial growth compared to inhibition with the vehicle alone is statistically significant. This measurement can be made directly from cultures isolated from body fluids or sites, or indirectly by assessing survival rates of infected animals.

For assessment of antibacterial activity of candidate peptide analogs and derivatives as compared to natural peptides, several animal models are available, such as acute infection models including those in which (a) normal mice receive a lethal dose of microorganisms, (b) neutropenic mice receive a lethal dose of microorganisms, or (c) rabbits receive an inoculum of microorganisms in the heart, and chronic infection models. The model selected will depend, in part, on the intended clinical indication of the peptide and/or analog or derivative thereof.

By way of example and not limitation, a normal mouse model is used to inoculate mice, intraperitoneally (i.p.) or intravenously (i.v.), with a lethal dose of bacteria. Typically, the dose is such that 90-100% of animals the within 2 days. The choice of a microorganism-strain for this assay depends, in part, upon the intended application of the peptide or analog or derivative thereof, and in the accompanying examples, assays are carried out with three different *Staphylococcus* strains. Briefly, shortly before or after inoculation with the microorganism of choice (generally within 60 minutes), peptides or analogs or derivatives thereof in a suitable formulation buffer (as described herein) is injected. Multiple injections of peptides may be administered. Animals are observed for up to 8 days post-infection, and the survival of animals is recorded. Successful treatment either rescues animals from death or delays death to a statistically significant level, as compared with non-treatment, control animals. Antimicrobial and/or anti-inflammatory peptide analogs or derivatives thereof that show better efficacy than the natural peptides, such as indolicidins, are preferred.

Furthermore, for in vivo use, low immunogenicity is preferred. To measure immunogenicity, peptides are injected into normal animals, generally rabbits. At various times after single or multiple injections, serum is obtained and tested for antibody reactivity to the peptide or analog or derivative thereof. Antibodies to peptides or analogs or derivatives thereof may be identified by ELISA, immunoprecipitation assays, western blots, and other methods known in the art (see *Antibodies: A Laboratory Manual*, 1988). In a preferred embodiment the antibody of interest has undetectable, or minimally detectable, reactivity with the candidate peptides or analogs or derivatives thereof. In addition, pharmacokinetics of the candidate peptides or analogs or derivatives in animals and histopathology of animals treated with the peptides may be determined.

For assessment of anti-inflammatory activity of candidate peptide analogs and derivatives as compared to natural peptides, a mouse model may be used. In one embodiment, a mouse model of oxazolone-induced contact hypersensitivity is used, as is known in the art and described herein. Briefly, a 3.0% (w/v) solution of oxazolone in acetone/corn oil (5:1) is applied topically to the skin on the shaved abdomens of mice of approximately the same weight and approximately the same age of day 0. On day 5, the mice are challenged with a 1% (w/v) oxazolone solution in acetone applied to the dorsal area of one ear (the other ear is the control), and 1 h later treated with a peptide formulation or formulation without peptide. Twenty-four hours later a dermal biopsy punch of the treated ear is taken and weighed. An increase in weight of the challenged ear compared to a control ear indicates an inflammatory response (see, e.g., *CRC Handbook of Toxicology*, Preclinical Immunotoxicity Assessment: Delayed Type Hypersensitivity, page 303, M. J. Derelanko and M. A. Hollinger, eds., CRC Press LLC, 1995).

In another embodiment to assess the anti-inflammatory activity of candidate peptide analogs and derivatives as compared to natural peptides, a mouse model of 12-o-tetradecanoylphorbol (TPA)-induced ear edema is used, as is known in the art and described herein. Briefly, a 0.005% solution of TPA in acetone is applied topically to the dorsal area of one ear (the other ear is the control). Immediately, the ear is treated with a peptide formulation or formulation without peptide. An increase in weight of the challenged ear compared to a control ear indicates an inflammatory response (see e.g., Young et al., *J. Invest. Dermatol.* 80:48, 1982; and Lloret and Moreno, *Biochem. Pharmacol.* 50:347, 1995).

In yet another embodiment, the anti-inflammatory activity of candidate peptide analogs and derivatives as compared to natural peptides may be assessed by examining cytokine production and proliferation of activated peripheral blood lymphocytes (PBLs). Briefly, human PBLs are collected from a subject and plated at $10^6$ cells/ml in serum free lymphocyte growth medium, stimulated with 10 µg/ml phytohemagglutinin (PHA) in the presence or absence of the candidate peptide. The PBLs are incubated at 37° C. at 5% $CO_2$ for 48 h, at which point the supernatants were collected. An ELISA is performed on the supernatants to detect a cytokine of interest (e.g., IL-1, TNF-α, IFN-γ) and the cells are incubated for another 72 h to measure proliferation (see, e.g., Sigusch et al., *J. Peridontol.* 69:1098, 1998).

Selection of antimicrobial and/or anti-inflammatory peptides and analogs or derivatives thereof as potential therapeutics is typically based on in vitro and in vivo assay results. In general, peptides that exhibit low immnogenicity, good in in vivo stability, and high efficacy at low dose levels are preferred candidate peptides and analogs or derivatives thereof. In addition, those peptides that exhibit statistically significant anti-inflammatory activity are also preferred.

IV. Peptide Formulations and Therapeutic Uses

As noted above, the present invention provides methods for treating and preventing infections by administering to a patient a therapeutically effective amount of an antimicrobial and/or anti-inflammatory peptide, preferably an indolicidin or analog or derivative thereof, as described herein. The peptide is preferably part of a pharmaceutical composition when used in the methods of the present invention. The pharmaceutical composition will include at least one of a pharmaceutically acceptable vehicle, carrier, diluent, or excipient, in addition to one or more antimicrobial and/or anti-inflammatory peptide and, optionally, other components. Pharmaceutically acceptable excipients for therapeutic use are well known in the pharmaceutical art, and are described herein and described, for example, in *Remington's Pharmaceutical Sciences*, Mack Publishing Co. (A. R. Gennaro, ed., 18$^{th}$ Edition, 1990) and in *CRC Handbook of Food, Drug, and Cosmetic Excipients*, CRC Press LLC (S. C. Smolinski, ed., 1992).

The therapeutic efficacy of a peptide composition according to the present invention is based on a successful clinical outcome and does not require 100% elimination of the microorganisms involved in the infection. Achieving a level of antimicrobial and/or anti-inflammatory activity at the site of infection that allows the host to survive, resolve the infection, or eradicate the causative agent is sufficient. When host defenses are maximally effective, such as in an otherwise healthy individual, only a minimal antimicrobial and/or anti-inflammatory effect may suffice. Thus, for anti-microbial activity, reducing the organism load by even one log (a factor of 10) may permit the defenses of the host to control the infection. In addition, clinical therapeutic success may depend more on augmenting an early bactericidal effect rather than on a long-term effect because this allows time tor activation of host defense mechanisms. This is especially true for life-threatening infections (e.g., meningitis) and other serious chronic infections (e.g., infective endocarditis). Similarly, the anti-inflammatory activity could aid in keeping excessive host defense mechanism reactions from causing additional damage.

The formulations of the present invention, having an amount of an antimicrobial and/or anti-inflammatory peptide sufficient to treat, prevent, or ameliorate an infection or inflammation are, for example, particularly suitable for topical (e.g., creams, ointments, skin patches, eye drops, ear drops, shampoos) application or administration. Other typical routes of administration include, without limitation, oral, parenteral, sublingual, bladder wash-out, vaginal, rectal, enteric, suppository, nasal, and inhalation. The term parenteral, as used herein, includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques. The pharmaceutical compositions of the present invention are formulated to allow the antimicrobial and/or anti-inflammatory peptide contained therein to be bioavailable upon administration of the composition to a subject. The level of peptide in serum and other tissues after administration can be monitored by various well-established techniques, such as bacterial, chromatographic or antibody based (e.g., ELISA) assays. Thus, in certain preferred embodiments, antimicrobial and/or anti-inflammatory peptides and analogs and derivatives thereof, as described herein, are formulated for topical application to a target site on a subject in need thereof such as an animal or a human.

The compositions may be administered to a subject as a single dosage unit (e.g., a tablet, capsule, or gel), and the compositions may be administered as a plurality of dosage units (e.g., in aerosol form). For example, the antimicrobial and/or anti-inflammatory peptide formulations may be sterilized and packaged in single-use, plastic laminated pouches or plastic tubes of dimensions selected to provide for routine, measured dispensing. In one example, the container may have dimensions anticipated to dispense 0.5 ml of the antimicrobial and/or anti-inflammatory peptide composition (e.g., a gel form) to a limited area of the target surface on or in a subject to treat or prevent an infection. A typical target, for example, is in the immediate vicinity of the insertion site of an intravenous catheter or intraarticularly at the joint that has arthritis.

An antimicrobial and/or anti-inflammatory peptide composition may be provided in various forms, depending on the amount and number of different pharmaceutically acceptable excipients present. For example, the peptide opposition may be in the form of a solid, a semi-solid, a liquid, a lotion, a cream, an ointment, a cement, a paste, a gel, or an aerosol. In a preferred embodiment, the peptide formulation is in the form of a gel. The pharmaceutically acceptable excipients suitable for use in the peptide formulation compositions as described herein may include, for example, a viscosity-increasing agent, a buffering agent, a solvent, a humectant, a preservative, a chelating agent, an oleaginous compound, an emollient, an antioxidant, an adjuvant, and the like. The function of each of these excipients is not mutually exclusive within the context of the present invention. For example, glycerin may be used as a solvent or as a humectant or as a viscosity-increasing agent. In one preferred embodiment, the formulation is a composition comprising an antimicrobial and/or anti-inflammatory peptide, a viscosity-increasing agent, and a solvent, which is useful, for example, at a target site having inflammation and/or an infection associated with an implanted or indwelling medical device, as described herein.

Solvents useful in the present compositions are well known in the art and include without limitation water, glycerin, propylene glycol, isopropanol, ethanol, and methanol. In some embodiments, the solvent is glycerin or propylene glycol, preferably at a concentration ranging from about 0.1% to about 20%, more preferably about 5% to about 15%, and most preferably about 9% to 11%. In other embodiments, the solvent is water or ethanol, preferably at a concentration up to about 99%, more preferably up to about 90%, and most preferably up to about 85%. (Unless otherwise indicated, all percentages are on a w/w basis.) In yet other embodiments, the solvent is at least one of water, glycerin, propylene glycol, isopropanol, ethanol, and methanol, preferably is glycerin or propylene glycol and ethanol, more preferably is glycerin and ethanol, and most preferably is glycerin and water. One embodiment is a composition comprising a antimicrobial and/or anti-inflammatory peptide, a viscosity-increasing agent, a solvent, wherein the solvent comprises at least one of water at a concentration up to 99%, glycerin at a concentration up to 20%, propylene glycol at a concentration up to 20%, ethanol at a concentration up to 99%, and methanol at a concentration up to 99%.

Another useful pharmaceutical excipient of the present invention is a viscosity-increasing agent. In certain embodiments, the antimicrobial and/or anti-inflammatory peptide compositions of the present invention include a viscosity-increasing agent, including without limitation dextran, polyvinylpyrrolidone, methylcellulose, carboxymethyl cellulose, hydroxyethyl cellulose, hydroxypropyl methycellulose, and hydroxypropyl cellulose, and combinations thereof. In preferred embodiments, the viscosity-increasing agent is hydroxyethyl cellulose or hydroxypropyl methylcellulose, preferably at a concentration ranging from about 0.5% to about 5%, more preferably, from about 1% to about 3%, most preferably from about 1.3% to about 1.7%. In yet other preferred embodiments, the peptide compositions have a first viscosity-increasing agent, such as hydroxyethyl cellulose, hydroxypropyl methylcellulose, dextran, or polyvinylpyrrolidone, and a second viscosity-increasing agent such as hydroxyethyl cellulose, hydroxypropyl methylcellulose, dextran, or polyvinylpyrrolidone. When used as either a first or second viscosity-increasing agent, dextran and polyvinylpyrrolidone are preferably used at a concentration ranging front about 0.1% to about 5% and more preferably from about 0.5% to about 1%. In one preferred embodiment, the first viscosity-increasing agent is hydroxyethyl cellulose at a concentration up to 3% and the second viscosity-increasing agent is hydroxypropyl methylcellulose at a concentration up to 3%. As is known in the art, the amount of viscosity-increasing agent may be increased to shift the form of the composition from a liquid to a gel to a semi-solid form. Thus, the amount of a viscosity-increasing agent used in a formulation may be varied depending on the intended use and location of administration of the peptide compositions provided herein.

In certain applications, it may be desirable to maintain the pH of the peptide composition contemplated by the present invention within a physiologically acceptable range and within a range that optimises the activity of the peptide or analog or derivative thereof. For example, the cationic peptides of the present invention function best in a composition that is neutral or somewhat acidic, although the peptides will still have antimicrobial and anti-inflammatory activity in a composition that is slightly basic (i.e., pH 8). Accordingly, a composition comprising a peptide, a viscosity-increasing agent, and a solvent, may further comprise a buffering agent. In certain embodiments, the buffering agent comprises a monocarboxylate or a dicarboxylate, and more specifically may be acetate, fumarate, lactate, malonate, succinate, or tartrate. Preferably, the peptide composition including the buffering agent has a pH ranging from about 3 to about 8, and more preferably front about 3.5 to about 7. In another preferred embodiment, the buffering agent is at a concentration ranging from about 1 mM to about 200 mM, and more preferably from about 2 mM to about 20 mM, and most preferably about 4 mM to about 6 mM.

Other optional pharmaceutically acceptable excipients are those that may, for example, aid in the administration of the formulation (e.g., anti-irritant, polymer carrier, adjuvant) or aid in protecting the integrity of the components of the formulation (e.g., anti-oxidants and preservatives). Additionally, for example, a 1.0% cationic peptide composition may be stored at 2° C. to 8° C. In certain embodiments, the composition comprising a peptide, a viscosity-increasing agent, and a solvent, may further comprise a humectant (preferably sorbitol, glycerol, and the like) or a preservative (preferably benzoic acid, benzyl alcohol, phenoxyethanol, methyl paraben, propylparaben, and the like). As used herein, any reference to an acid may include a free acid, a salt, and any ester thereof. In other embodiments, any of the aforementioned compositions further comprise a humectant and a preservative. In certain circumstances, the peptide or analog or derivative thereof may itself function as a preservative of the final therapeutic composition. For example, a preservative is optional in the gel formulations described herein because the gels may be sterilised by autoclaving and, furthermore, show the surprising quality of releasing (i.e., making bioavailable) a peptide at a more optimal rate than other formulations, such as a cream. In addition, particular embodiments may have in a single formulation a humectant, a preservative, and a buffering agent, or combinations thereof. Therefore, a preferred embodiment is a composition comprising a peptide, a viscosity-increasing agent, a solvent, a humectant, and a buffering agent. Another preferred embodiment is a composition comprising a peptide, a viscosity-increasing agent, a buffering agent, and a solvent. In yet another preferred embodiment, the composition comprises a peptide, a buffering agent, and a solvent. Each of the above formulations may be used to treat prevent, or ameliorate infection, to reduce the microflora at a target site such as a catheter insertion site on a subject (i.e., animal or human), or to reduce inflammation at a target site.

In yet other embodiments, the composition is in the form of an ointment comprising an antimicrobial and/or anti-inflammatory peptide (preferably in an amount sufficient to treat or prevent an infection) and an oleaginous compound. For example, oleaginous compound may be petrolatum. In one embodiment, the oleaginous compound is present at a concentration ranging from about 50% to about 100%, more preferably from about 70% to about 100%, even more preferably from about 80% to about 100%, and most preferably from about 95% to about 100%. In certain other embodiments, the ointment composition may further comprise at least one emollient. The emollients may be present at a concentration ranging from about 1% to about 40%, more preferably from about 5% to about 30%, and more preferably from about 5% to about 10%. In certain preferred embodiments, the emollient may be mineral oil, cetostearyl alcohol, glyceryl stearate, and a combination thereof.

In another aspect the composition may be in the form of a semi-solid emulsion (e.g., a cream) comprising an antimicrobial and/or anti-inflammatory peptide (preferably in an amount sufficient to treat or prevent an infection), a solvent, a buffering agent, at least one emollient, and at least one emulsifier. In a preferred embodiment, the semi-solid emulsion or cream further comprises at least one of a humectant (e.g., sorbitol and/or glycerin), an oleaginous compound (e.g., petrolatum), a viscosity increasing agent (e.g., dextran, polyvinylpyrrolidone, hydroxyethyl cellulose, and/or hydroxypropyl methylcellulose), an antioxidant (e.g., butylated hydroxytoluene and preferably at a concentration ranging from about 0.01% to about 0.1%), a preservative (e.g., benzoic acid, benzyl alcohol, phenoxyethanol, methyparaben, propylparaben, or a combination thereof), or a combination thereof. In certain preferred embodiments, the emollient may be one or more of stearyl alcohol, cetyl alcohol, and mineral oil. In certain other preferred embodiments, the emulsifiers may be one or more of stearyl alcohol, cetyl alcohol, polyoxyethylene 40 stearate, and glyceryl monostearate. In a preferred embodiment, the emulsifier is present, at a concentration ranging from about 1% to about 20%, more preferably from about 5% to about 10, and most preferably from about 1% to about 1.5%. As noted above, the function of each of these emulsifiers and emollients is not mutually exclusive in that an emollient may function as an emulsifier and the emulsifier may function as an emollient, depending on the particular formulation, as is known in the art and is described herein. In certain preferred embodiments the solvent comprises water and the like, and the buffering agent comprises a monocarboxylate or dicarboxylate and the like, as described herein.

A subject suitable for treatment with a peptide formulation may be identified by well-established indicators of risk tor developing a disease or well-established hallmarks of an existing disease. For example, indicators of an infection include fever, pus, microorganism positive cultures, inflammation, and the like. Infections that may be treated with peptides provided by the present invention include without limitation those caused by or due to microorganisms, whether the infection is primary, secondary, opportunistic, or the like. Examples of microorganisms include bacteria (e.g., Gram-positive, Gram-negative), fungi, (e.g., yeast and molds), parasites (e.g., protozoans, nematodes, cestodes and trematodes), viruses (e.g., HIV, HSV, VSV), algae, and prions. Specific organisms in these classes are well known (see, for example, Davis et al., *Microbiology*, $3^{rd}$ edition, Harper & Row, 1980, and Stanier et al., *The Microbial World*, $5^{th}$ edition, Prentice Hall, 1986). Infections include, but are not limited to, toxic shock syndrome, diphtheria, cholera, typhus, meningitis, whooping cough, botulism, tetanus, pyogenic infections, sinusitis, pneumonia, gingivitis, mucitis, folliculitis, cellulitis, acne and acne vulgaris, impetigo, osteomyelitis, endocarditis, ulcers, burns, dysentery, urinary tract, infections, gastroenteritis, anthrax, Lyme disease, syphilis, rubella, septicemia, and plague; as well as primary, secondary, and opportunistic directions associated with, for example, trauma, surgery, endotracheal intubation, tracheostomy, and cystic fibrosis.

A subject may have other clinical indications that have associated infection or inflammation treatable or preventable with the compositions and methods of the present invention, which include without limitation those associated with implantable, indwelling, or similar medical devices, such as intravascular catheters (e.g., intravenous and intraarterial), right heart flow-directed, catheters, Hickman catheters, arteriovenus fistulae, catheters used in hemodialysis and peritoneal dialysis (e.g., silastic, central venous, Tenckhoff, and teflon catheters), vascular access ports, indwelling urinary catheters, urinary catheters, silicone catheters, ventricular catheters, synthetic vascular prostheses (e.g., aortofemoral and femoropopliteal), prosthetic heart valves, prosthetic joints, orthopedic implants, penile implants, shunts (e.g., Scribner, Torkildsen, central nervous system, portasystemic, ventricular, ventriculoperitoneal), intrauterine devices, tampons, contact lenses, dental implants, ureteral stents, pacemakers, implantable defibrillators, tubing, cannulas, probes, blood monitoring devices, needles, and the like. As used herein, "medical device" refers to any device for use in a subject, such as an animal or human.

An advantage of the present invention is that antisepsis of a target site for device insertion with an indolicidin or analog or derivative thereof, and formulated as described herein, may be achieved prior to device insertion and/or after device insertion and in combination with barrier precautions, which will reduce the risk of device-associated infections and inflammation. Therefore, the compositions and methods of the present invention are specifically useful, for example, for cutaneous antisepsis to treat, prevent, or ameliorate localized infection and/or inflammation (e.g., after trauma, surgery, or other medical procedure), and to prevent medical device-related septicemia. Furthermore, one benefit of using, for example, cationic peptides is to reduce the risk of selecting antimicrobial-resistant microorganisms.

By way of background and as noted above, inflammation is the body's reaction to invasion by an infectious agent, antigen challenge, or even just physical, chemical or traumatic damage. The mechanism for triggering the response of the body to injury is extremely sensitive. Thus, the body has the capacity to respond to both minor injuries such, as bruising, scratching, cuts, and abrasions, as well as to major injuries such as severe burns and amputation of limbs. Damage may breach the integrity of the skin or internal surfaces and affect underlying connective tissue, muscle, and blood vessels. In this situation infection can, and frequently does result, because the normal barrier to the entry of harmful organisms has been broken. The cells of the immune system are widely distributed throughout the body, but if infection or tissue damage occurs, the body must concentrate the immune response at the site of damage. To minimize the possibility of self-damage to tissue surrounding the site of damage, inflammatory responses must be well ordered and controlled. The body must be able to act quickly in some situations, such as to reduce or stop the loss of blood, whereas tissue repair and reconstruction can be delayed. Therefore, a wide variety of interconnected cellular and humoral (soluble) mechanisms are activated when tissue damage and injection occur.

There are endogenous and exogenous factors capable of inducing damage to cells and tissues. Exogenous factors include, without limitation, mechanical (traumatic injury), physical (extremely low or high temperature, ionising irradiation, microwaves), chemical (caustic agents, poisons, venoms, genotoxic and proteotoxic compounds), nutritive (deficiency of oxygen, vitamins and basic nutrients), and biological (viruses, microorganisms, protozoan and metazoan parasites). The peptides and pharmaceutical compositions thereof as described herein are useful as an anti-inflammatory agent for treating, preventing, and ameliorating damage caused by these endogenous and exogenous factors. In certain embodiments, the peptides and pharmaceutical compositions of the present invention are used in methods to treat, prevent, and ameliorate inflammatory diseases, as described herein. Preferably, the peptide formulations, alone or in combination with antibiotic and/or anti-inflammatory agents, are used. In a method to treat, prevent, or ameliorate clinical indications such as acne, arthritis, autoimmune disease, burn, Crohn's disease, colitis, contact hypersensitivity, delayed type hypersensitivity, eczema, endotoxin shock syndrome, fibromyositis, graft rejection, lichen, microbial infection, multiple sclerosis, parapsoriasis, psoriasis, sclerosis, and seborrhea.

Endogenous damaging factors include immunopathological reactions, and some neurological and genetic disorders. However, exogenous antigens may also trigger immunopathological reactions. Genetically caused alterations leading to inflammation are exemplified by destruction of membrane structures, by derangement of transport mechanisms, and by defective metabolic or mediator activity. (e.g., metabolic intermediates such as different free radicals, aldehydes, and ketones may accumulate). Similarly, during an immune response, effector cells and molecules participating in immune mechanisms may damage the host, which are thought to be the immunopathological responses (i.e., chronic inflammation). As is known in the art, there are many different kinds of inflammation, such as acute and chronic inflammation. In certain preferred embodiments, the peptides and analogs or derivatives thereof of the present invention are used in a method to treat, prevent, or ameliorate inflammation wherein the inflammation, may be acute, adhesive, atrophic, catarrhal, chronic, croupous, degenerative, exudative, fibrinopurulent, fibrinous, granulomatous, interstitial, necrotic, proliferative, pseudomembranous, purulent, sclerosing, serofibrinous, serous, and subacute.

Uses of peptides and analogs or derivatives thereof of the present invention encompass numerous applications where a topical antimicrobial or anti-inflammatory agent is useful in the treatment, prevention, or amelioration of infection and/or inflammation. For example, type I hypersensitivity is characterized by an allergic reaction that occurs immediately following contact with an allergen. In some individuals, certain allergens have a propensity to stimulate production of IgE antibodies, which bind nonspecifically to mast cells and basophils. Subsequent attachment of antigen to the cell-bound IgE antibodies results in release of cytoplasmic granule contents (e.g., histamine), and in the synthesis and secretion of biologically active products of arachidonic acid (e.g., leukotrienes). Reaginic reactions are responsible for such allergic phenomena as urticaria, seasonal rhinitis, asthma, and atopic dermatitis (e.g., atopic diseases). In settings where large amounts of allergens enter the host circulation, systemic anaphylaxis may arise with manifestations ranging from urticaria to angioedema (swelling of mucous membranes, for example, of the lips, tongue, palate, and larynx), nausea and vomiting (edema and smooth muscle contraction of gastrointestinal tract), asthma (bronchial smooth muscle contraction), and hypotension (increased vascular permeability resulting in a loss of blood volume into tissue and thus a fall in blood pressure; reducing contractility of the heart also contributes to hypotension). Life-threatening reactions involve laryngeal edema, severe asthma, or severe hypotension and circulatory collapse. Exogenous agents that induce IgE-mediated anaphylaxis include, without limitation, penicillin, insect venoms, foods, and occasionally immunotherapy (i.e., injection of an allergen to which a person is allergic to treat allergic disease). Preferably, a peptide formulation, alone or in combination with antibiotic and/or anti-inflammatory agents, is administered orally and most preferably by inhalation. Systemic administration could also be via intravenous, intramuscular or subcutaneous injections or infusions.

Similarly, another use for the present compositions and methods would be in the treatment of immunopathological reactions resulting from type II hypersensitivity. Type II, or antibody-dependent cytotoxic hypersensitivity, occurs when antibody binds to wither self-antigen or foreign antigen on cells, and leads to phagocytosis, killer cell activity or complement-mediated lysis. The type II reactions involve IgG and IgM antibodies directed to antigens on the surface of specific cells and tissues; therefore, the damage caused by type II reactions tends to be localized. These hypersensitivity reactions are related to normal immune responses seen against microorganisms and larger multicellular parasites. Indeed, in mounting a reaction to a pathogen, exaggerated immune reactions may sometimes be as damaging to the host as the effects of the pathogen itself. In type II hypersensitivity, antibodies bind cell surface antigens of target cells to form an immune complex, which complex will either interact with complement or an effector cell to bring about damage to the target cell. Antibodies that bind to tissue antigens will interact with complement by activating the classical pathway, which results in the lysis cells by a membrane attack complex. Alternatively, antibodies may link target cells to effector cells (e.g., macrophages, neutrophils, and eosinophils), which results in antibody-dependent cell-mediated cytotoxicity (ADCC). By enhancing the lysosomal activity of phagocytes, and potentiating their capacity to produce reactive oxygen intermediates, the antibodies increase the probability of immunopathological damage in hypersensitivity reactions.

For example, neutrophils from the synovial fluid of patients with rheumatoid arthritis produce more superoxide when stimulated than do neutrophils from peripheral blood. Thus, activation of neutrophil's in the rheumatoid joint may be due to mediators such as the immune complexes and complement fragments described above. There are three main subtypes of cytotoxic hypersensitivity, which are as follows: (1) isoimmunization, which are reactions between members of the same species (e.g., blood transfusion reactions, newborn hemolytic disease, transplantation rejections); (2) autoimmune type II hypersensitivity reactions are evoked by antibodies in the host directed against self antigens (autoantibodies) (e.g., autoimmune hemolytic anemia, Hashimoto's thyroiditis, idiopathic thrombocytopenic purpura, Goodpasture's syndrome); and (3) drug reactions may result from drugs coupled to body components that undergo conversion from a hapten to a full antigen, which may sensitive certain individuals (e.g., hemolytic anemia associated with continued administration of chlorpromazine or phenacetin, agranulocytosis associated with the taking of amidopyrine or of quinidine, thrombocytopenic purpura). In a preferred embodiment, inflammation associated with a type II hypersensitivity reaction, such as graft rejection, is treated, prevented, or ameliorated with systemically or topically administered antimicrobial and/or anti-inflammatory peptide compositions, as described herein.

A further use for the present compositions and methods would be in the treatment, prevention, or amelioration of inflammation associated with type III hypersensitivity reactions. Type III hypersensitivity develops when immune complexes are formed in large quantities, or cannot be cleared adequately by the reticuloendothetial system, leading to serum-sickness type reactions. Deposition of immune complexes in local tissues with resultant inflammation is common in rheumatic diseases. Such complexes may localize to small vessels, resulting in local inflammation and vasculitis. Phagocytosis of immune complexes by macrophages can result in release of cytokines, such as IL-1 and TNF-α, which initiate fever. Deposition of immune complexes in the glomerular basement membrane can lead to glomerulitis. Arthritis may result from similar mechanisms; rheumatoid arthritis has many characteristics of a local immune complex reaction, whereas systemic lupus erythematosus has many clinical features of serum sickness.

One example of type III hypersensitivity reactions are those that develop from low-grade persistent infection (such as occur with α-hemolytic Streptococcus viridans or Staphylococcal infective endocarditis, or with a parasite such as Plasmodium vivax, or in viral hepatitis), together with a weak antibody response, which leads to chronic immune complex formation with the eventual deposition of complexes in the tissues. Another example is when the mononuclear phagocyte, erythrocyte, and complement systems (which are responsible for the removal of complexes) become overloaded, the complexes are deposited in the tissues as occurs in systemic lupus erythematosus. Yet another example of type III hypersensitivity is extrinsic allergic alveolitis (e.g., Farmer's lung, Pigeon fancier's lung), which arises inhalation of antigenic material from moulds, plants or animals. In a preferred embodiment, the peptide compositions described herein are used in a method for treating, preventing, or ameliorating inflammation by parenterally administering a composition comprising a buffering agent a solvent, and an indolicidin analog of up to 35 amino adds, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In another preferred embodiment there is administered a composition comprising a pharmaceutically acceptable diluent and an indolicidin analog of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157.

An additional use for the present peptide compositions and methods would be in the treatment of type IV hypersensitivity reactions. Type IV, or delayed type hypersensitivity (DTH), is most seriously manifested when antigens (e.g., those of Mycobacterium tuberculosis) are trapped in a macrophage and cannot be cleared. T cells are then stimulated to elaborate lymphokines, which mediate a range of inflammatory responses. Other aspects of DTH reactions are seen in graft rejection and allergic contact dermatitis. DTH is used as a general category to describe all those hypersensitivity reactions which take more than 12 hours to develop and which involve cell-mediated immune reactions rather than humoral immune reactions. Whereas allergic reactions occur within seconds and minutes, and immune complex reactions occur within several hours to one day, DTH reactions peak at 2 to 3 days. Contact hypersensitivity (e.g., contact dermatitis, which is caused by sensitization to certain simple chemicals) and tuberculin-type hypersensitivity both occur within 72 hours of antigen challenge, whereas granulomatous reactions develop over a period of weeks. In some cases, such as chronic granulomatous disease of childhood, granuloma formation can lead to obstruction of vital structures (e.g., esophagus or ureter). The DTH reactions are probably important for host defense against intracellular parasites, such as M. tuberculosis, certain viruses, and in certain diseases, such as sarcoidosis, Wegener's granulomatosis, and polymyositis. In a preferred embodiment, inflammation associated with a type IV hypersensitivity reaction, such as contact dermatitis, is treated, prevented, or ameliorated with systemically or topically administered peptide compositions, as described herein.

Another use for the present compositions and methods would be in the treatment of burn wounds, with associated acute inflammation, which remain the most common cause of morbidity and mortality in extensively burned patients. Moreover, infection is the predominant determinant of wound healing, incidence of complications, and outcome of burn patients. The main organisms responsible are Pseudomonas aeruginosa, S. aureaus, Streptococcus pyogenes, and various gram-negative organisms. Frequent debridements and establishment of an epidermis or a surrogate, such as a graft or a skin substitute, is essential for prevention of infection. Preferably, the peptide formulations, alone or in combination with antibiotic and/or anti-inflammatory agents, is applied to burn wounds as a gel, ointment or cream, and/or administered systemically. Topical application may prevent systemic infection following superficial colonization or eradicate a superficial infection. An antimicrobial and/or anti-inflammatory peptide composition is preferably administered as a 0.5 to 2% gel, cream, or ointment, as described herein. Application to the skin could be done once a day or as often as dressings are changed. Systemic administration could be via intravenous, intramuscular or subcutaneous injections or infusions. Other routes of administration known in the art could also be used.

Still another use tor the present compositions and methods would be in in the treatment of surgical wounds, especially those associated with foreign material (e.g., sutures). Nosocomial infections may occur in as many as 71% of all surgical patients, and 40% of those are infections at the operative site. Despite efforts to prevent infection, it is estimated that between 500,000 and 920,000 surgical wound infections complicate the approximately 23 million surgical procedures performed annually in the United States. The infecting organisms are varied, but Staphylococci spp. are important organisms in these infections. Preferably, the peptide formulations, alone or in combination with antibiotics, is applied as an gel, ointment, cream or liquid to the wound site, or as a liquid in the wound prior to and during closure of the wound. Following closure, the peptide compositions of the instant invention could also be applied at dressing changes. For surgical or trauma wounds that are infected, the peptide formulations described herein may be applied topically and/or systemically.

In yet another example, sterile gauze dressing has been the standard of care in catheterization for many years, but it has also been demonstrated that transparent polyurethane film dressings are superior because they permit continuous inspection of the catheterization site, they secure the device reliably, and they permit the patients to bathe and shower without saturating the dressing. Therefore, certain preferred embodiments include peptide compositions as described herein for use with sterile gauze or polyurethane film dressings to minimize infection and inflammation.

Additionally, the compositions and methods of the present invention may be used to reduce the risk of device-related infections and inflammation by directly coating a medical device prior to insertion at a target site or by impregnating the external surface of a medical device at the time of manufacture. In yet another aspect of this invention, the formulation includes a peptide or peptide composition suitable for impregnating or coating a medical device. Thus, an antimicrobial and/or anti-inflammatory peptide of this invention may be formulated as a coating or impregnation material suitable for treating the surfaces of a medical device or its components. In certain embodiments, such coatings and impregnation materials may include covalent and/or non-covalent attachment of a peptide and analog or derivative thereof, to the interior and/or exterior surfaces of a medical device or its components. In other embodiments, such a coating and impregnation material may include the entrapment of a peptide in a hydrogel layer or a bioerodable layer.

Other embodiments include use of peptide coatings, gels, ointments, and impregnation compositions alone or in conjunction, with fiber units or catheter components used with, for example, a hemodialysis apparatus. In one embodiment, an arteriovenous shunt, such as a Scribner shunt, may be impregnated, coated, or adapted to a filter containing an antimicrobial and/or anti-inflammatory peptide. Other embodiments include the same coatings, gels, ointments, and impregnation, compositions for use with an arteriovenous fistula. In still another embodiment, a coating may be suitable for use with a woven fiber vascular shunt.

Still other embodiments include use of peptide formulations and methods with temporary access sites used to insert a medical device. In one preferred embodiment, peptide formulations may be used during a femoral vein catheterization. Other preferred embodiments include use of the peptide formulations with catheters, such as vascular dialysis catheters, pulmonary artery catheters, peritoneal dialysis catheters, umbilical catheters, and subclavian vein catheters.

By way of example and not limitation, both local and systemic infection and inflammation may result from contaminated intravascular devices, such as a CVC, and the organisms typically responsible are coagulase-negative *Staphylococci* (CoNS), *Staphylococcus aureus, Enterococcus* spp, *E. coli* and *Candida* spp. Hence, an antimicrobial and/or inflammatory peptide or analog or derivative thereof, preferably in the form of a gel or cream, may be applied to the catheter site prior to insertion of the catheter and then again at each dressing change. Preferably, the peptide is at a concentration ranging from about 0.85% to about 1.15%. Therefore, in a typical embodiment, a compositions contains an antimicrobial and/or anti-inflammatory peptide at a concentration ranging from about 0.01% to about 10%; a viscosity-increasing agent selected of dextran, polyvinylpyrrolidone, hydroxyethyl cellulose, a hydroxypropyl methylcellulose; and a solvent of water, glycerin, propylene glycol, isopropanol, ethanol, or methanol; and at a pH ranging from about 3 to about 8.

In a preferred embodiment, the present invention is useful in a method for reducing microflora at a target site, comprising applying to the target site a composition comprising an antimicrobial and/or anti-inflammatory peptide, a viscosity-increasing agent, and a solvent. As used herein, a target site is any site on a subject where there is present, or there is a risk of, a primary or secondary or opportunistic infection (which infection is outside or inside the subject), and is any site where a formulation of the present invention may be administered or applied. In certain embodiments, the microflora being reduced at the reduced site may be prokaryotic, eukaryotic, or viral, and preferably a prokaryotic. In other embodiments, the method for reducing microflora at a target site, comprises applying to the target site a composition containing peptide, a viscosity-increasing agent, and a solvent, and further comprises inserting a medical device at the target site before and/or after applying the composition. In another embodiment, the composition may further contain a buffering agent as described above and may have a pH ranging from about 3.5 to about 7. In addition, the composition may further contain a preservative, such as benzoic acid, benzyl alcohol, phenoxyethanol, methylparaben, propylparaben, and the like, and combinations thereof. Preferably, the peptide is an indolicidin or analog or derivative thereof, as described herein.

Another preferred embodiment is a composition comprising a viscosity-increasing agent, a solvent, and a peptide of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In a more preferred embodiment, the peptide is at a concentration ranging from about 0.8% to about 1.2%. Such compositions would be useful, for example, for topical or systemic administration. In another embodiment, the composition may be applied to a target site to treat, prevent, or ameliorate inflammation, such as inflammation associated with an implanted or indwelling medical device. Preferably, the composition is applied to a target site to treat, prevent, or ameliorate inflammation associated with a condition such as acne, arthritis, autoimmune, disease, burn, Crohn's disease, colitis, contact hypersensitivity, delayed type hypersensitivity, eczema, endotoxin shock syndrome, fibre myositis, graft rejection, lichen, microbial infection, multiple sclerosis, parapsoriasis, psoriasis, sclerosis, and seborrhea. In another embodiment, the composition is applied to a target site to treat, prevent, or ameliorate different types of inflammation, such as acute, adhesive, atrophic, catarrhal, chronic, croupous, degenerative, exudative, fibrinopurulent, fibrinous, granulomatous, interstitial, necrotic, proliferative, pseudomembranous, purulent, sclerosing, serofibrinous, serous, and subacute.

The compositions and methods of the present invention may be used therapeutically to effectively treat, prevent, or ameliorate acne, including severe acne vulgaris or acne varioliformis. Acne is due to colonization and infection of hair follicles and sebaceous cysts by *Propionibacterium acne*. Most cases remain mild and do not lead to scarring, although a subset of patients develop large inflammatory cysts and nodules, which may drain and result in significant scarring. The peptide formulations as described herein may be incorporated into soap, or applied topically as a cream, lotion, or gel to the affected areas. The peptide formulation may be applied either once a day or multiple times during the day, and the length of treatment may be for as long as the lesions are present or to prevent recurrent lesions. Alternatively, the peptide composition may be formulated to be administered orally or systemically to treat or prevent acne lesions. Preferably the peptide composition is formulated for topical administration or application. A preferred embodiment is a composition comprising a viscosity-increasing agent, a solvent, and a peptide of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. Another preferred embodiment is a composition comprising buffering agent, a solvent, and a peptide of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In a more preferred embodiment, the peptide is at a concentration ranging from about 0.8% to about 1.2%. In another preferred embodiment, the peptide composition may further comprise an acne medicament such as retinoid, vitamin D3, or corticosteroid, and analogs or derivatives thereof. Therefore, in certain preferred methods to reduce microflora or inflammation, or to treat or prevent an infection, at a target site, the target site may be skin, and the skin may further comprise acne.

Another example of the therapeutic value of the compositions and methods of the present invention would be in the treatment of nosocomial infections. For example, infection by *S. aureus* may result in impetigenous lesions or infected wounds, and is associated with increased infection rates following cardiac surgery, hemodialysis, orthopedic surgery and neutropenia, both disease-induced and iatrogenic. Nasal and extra-nasal carriage of *Staphylococci* spp. can result in hospital outbreaks of the same *Staphylococci* strain that is colonizing a patient's or a hospital worker's nasal passage or extra-nasal site. Much attention has been paid to the eradication of nasal colonization, but the results of treatment have been generally unsatisfactory. The use of topical antimicrobial substances, such as bacitracin, tetracycline, and chlorhexidine, results in the suppression of nasal colonization, as opposed to eradication.

Accordingly, a preferred embodiment is a composition comprising buffering agent, a solvent, and a peptide of up to 35 amino acids, comprising one of the following sequences: 11B7, 11B11, 11B24, 11B38, 11D21, 11F4, 11F11, 11F12, 11F17, 11F35, 11F43, 11F46, 11F60, 11F61, 11F65, 11F66, 11F82, 11F83, 11F110, 11J02, 11J30, 11J32, 11J33, 11J37, 11J44, 11J45, 11J67, 11J68, 11J84, 11J97, 11J105, 11J115, 11J131, 11J136, 11J148, or 11J157. In a more preferred embodiment, the peptide is at a concentration ranging from about 0.8% to about 1.2%, or ranging from about 2.5% to about 3.5%.

These preferred compositions may be used in a method for reducing microflora, or for treating or preventing infection, at a target site by applying to the target site the peptide foundations described herein. In another embodiment, the target site may be a mucosa, preferably the mucosa of the nasal passage or anterior naris. These preferred compositions might also be used in a method for treating, preventing or ameliorating inflammation at a target site by applying to the target site the peptide formulations described herein.

Pharmaceutical compositions of the present invention are administered in a manner appropriate to the infection or disease to be treated. The amount and frequency of administration will be determined by factors such as the condition of the patient, the cause of the infection, and the severity of the infection, or any other appropriate parameter known in the art. Appropriate dosages may be determined by clinical trials, but will generally range from about 0.1 to 50 mg/kg.

In addition, the compositions of the present invention may be used in the manner of common disinfectants or in any situation in which microorganisms or inflammation are undesirable. For example, these peptides may be used as surface disinfectants, coatings, including covalent bonding, for medical devices, coatings for clothing, such as to inhibit growth of bacteria or repel mosquitoes, in filters for air purification, such as on an airplane, in water purification, constituents of shampoos and soaps, food preservatives, cosmetic preservatives, media preservatives, herbicide or insecticides, constituents of building materials, such as in silicone sealant, and in animal product processing, such as curing of animal hides.

The peptides, particularly the labeled analogs and derivatives thereof, may be used in image analysis and diagnostic assays or for targeting sites in multicellular and single cellular organisms. As a targeting system, the analogues may be coupled with other peptides, proteins, nucleic acids, antibodies, chemical compounds (e.g., fluorescent tags), and the like.

The following Examples are provided by way of illustration and not by way of limitation.

EXAMPLES

Example 1

Synthesis, Purification, and Characterization of Peptides and Analogues

Peptide synthesis is based on the standard solid-phase Fmoc protection strategy. The instrument employed is a 9050 Plus Pepsynthesiser (PerSeptive BioSystems, Inc.). Polyethylene glycol polystyrene (PEG-PS) graft resins are employed as the solid phase derivatized with an Fmoc-protected amino acid linker for C-terminal amide synthesis. HATU (O-(7-azabenzotrialoze-1-yl)-1,1,3,3-tetramethyl-uronium hexafluorophosphate) is used as the coupling reagent. During synthesis, coupling steps are continuously monitored to ensure that each amino acid is incorporated in high yield. The peptide is cleaved from the solid-phase resin using trifluoroacetic acid and appropriate scavengers and the crude peptide is purified using preparative reversed-phase chromatography. Typically the peptide is prepared as the trifluoroacetate salt, but other salts, such as acetate, chloride and sulfate, can also be prepared by salt exchange.

All peptides are analyzed by mass spectrometry to ensure that the product has the expected molecular mass. The product should have a single peak accounting for >95% of the total peak area when subjected to analytical reversed-phase high performance liquid chromatography (RP-HPLC), a separation method that depends on the hydrophobicity of the peptide. In addition, the peptide should show a single band accounting for >90% of the total band intensity when subjected to acid-urea gel electrophoresis, capillary electrophoresis, or any other separation method based on the charge to mass ratio of a peptide.

Peptide content, the amount of the product that is peptide rather than retained water, salt or solvent, is measured by quantitative amino acid analysis, free amine derivatization or spectrophotometric quantitation. Amino acid analysis also provides information on the ratio of amino acids present in the peptide, which assists in confirming the authenticity of the peptide.

Peptide analogues and their names are listed below. In this list, and elsewhere, the amino acids are denoted by the one-letter amino acid code and lower case letters represent the D-form of the amino acid.

TABLE 1

| | Indolicidin analogs and derivatives thereof and Other Peptides |
|---|---|
| Apidaecin IA | G N N R P V Y I P Q P R P P H P R I |
| Deber A2KA2 | K K A A A K A A A A A K A A W A A K A A A K K K K |
| 10 | I L P W K W P W W P W R R |
| 10CN | I L P W K W P W W P W R R |
| 11 | I L K K W P W W P W R R K |
| 11CN | I L K K W P W W P W R R K |
| 11CNR | K R R W P W W P W K K L I |
| 11A1CN | I L K K F P F F P F R R K |
| 11A2CN | I L K K I P I I P I R R K |
| 11A3CN | I L K K Y P Y Y P Y R R K |
| 11A4CN | I L K K W P W P W R R K |
| 11A5CN | I L K K Y P W Y P W R R K |
| 11A6CN | I L K K F P W F P W R R K |
| 11A7CN | I L K K F P F W P W R R K |
| 11A8CN | I L R Y V Y Y V Y R R K |
| 11A9CN | I L R W P W W P W W P W R R K |
| 11A10CN | W W R W P W W P W R R K |
| 11B1CN | I L R R W P W W P W R R K |
| 11B2CN | I L R R W P W W P W R K |
| 11B3CN | I L K W P W W P W R R K |
| 11B4CN | I L K K W P W W P W R K |
| 11B5CN | I L K W P W W P W R K |
| 11B7CN | I L R W P W W P W R R K |
| 11B7CNR | K R R W P W W P W R L I |
| 11B8CN | I L W P W W P W R R K |
| 11B9CN | I L R R W P W W P W R R R |
| 11B10CN | I L K K W P W W P W K K K |
| 11B11CN | I L E E W P W W P W E E E |
| 11B16CN | I L R W P W W P W R R K I M I L K K A G S |
| 11B17CN | I L R W P W W P W R R K M I L K K A G S |
| 11B18CN | I L R W P W W P W R R K D M I L K K A G S |
| 11B19CN | I L R W P W R R W P W R R K |
| 11B20CN | I L R W P W W P W R R K I L M R W P W W P W R R K M A A |
| 11B24CN | I L T W P W W P W T T T |
| 11B32CNR | K R K W P W W P W R L I |
| 11B36CN | I L K V W W V W R R K |
| 11B38CN | I L Q W P W W P W Q Q Q |
| 11C3CN | I L K K W A W W P W R R K |
| 11C4CN | I L K K W P W W A W R R K |
| 11C5CN | W W K K W P W W P W R R K |
| 11D1CN | L K K W P W W P W R R K |
| 11D3CN | P W W P W R R K |
| 11D4CN | I L K K W P W W P W R R K M I L K K A G S |
| 11D5CN | I L K K W P W W P W R R M I L K K A G S |
| 11D6CN | I L K K W P W W P W R R I M I L K K A G S |
| 11D9M8 | W W P W R R K |
| 11D10M8 | I L K K W P W |
| 11D11H | I L K K W P W W P W R R K M |
| 11D12H | I L K K W P W W P W R R M |
| 11D13H | I L K K W P W W P W R R I M |
| 11D14CN | I L K K W W W P W R K |
| 11D15CN | I L K K W P W W W R K |
| 11D18CN | W R I W K P K W R L P K W |
| 11D19CN | C L R W P W W P W R R K |
| 11D21CN | I L R W P W W P W R R K |
| 11E1CN | i L K K W P W W P W R R K |
| 11E2CN | I L K K W P W W P W R R k |
| 11E3CN | i L K K W P W W P W R R k |
| 11F1CN | I L K K W V W V W R R K |
| 11F2CN | I L K K W P W W V W R R K |
| 11F3CN | I L K K W V W W P W R R K |
| 11F4CN | I L R W V W W V W R R K |
| 11F4CNR | K R R W V W W V W R L I |
| 11F5CN | I L R R W V W W V W R R K |
| 11F6CN | I L R W W V W W V W W R R K |
| 11F11CN | R L W V W W V W |
| 11F12CN | R L W V W W V W R R K |
| 11F17CN | R L W V W W V W R R |
| 11F50CN | R L G G W V W W V W R R |
| 11F56CN | R L W W V V W W R R |
| 11F60CN | R L W W Q Q W W R R |
| 11F63CN | R L V V W W V R R |
| 11F64CN | R L F V W W V F R R |
| 11F65CN | R L W V V V V W R R |
| 11F66CN | R L V V W V V W R R |
| 11F67CN | r L W V W W V W R R |
| 11F68CN | R L W V W W V W R r |

TABLE 1-continued

| \multicolumn{2}{c}{Indolicidin analogs and derivatives thereof and Other Peptides} |
|---|---|
| 11F82CN | R L L V W W V L R R |
| 11F83CN | R L G G G G G G R R |
| 11F93CN | W V R L W W R R V W |
| 11F110CN | R L V V W V V W R R K |
| 11G2CN | I K K W P W W P W R R K |
| 11G3CN | I L K K P W W P W R R K |
| 11G4CN | I L K K W W W P W R R K |
| 11G5CN | I L K K W P W W W R R K |
| 11G6CN | I L K K W P W W P R R K |
| 11G7CN | I L K K W P W W P W R R |
| 11G13CN | I L K K W P W W P W K |
| 11G14CN | I L K K W P W W P W R |
| 11G24CN | L W P W W P W R R K |
| 11G25CN | L R W W W P W R R K |
| 11G26CN | L R W P W W P W |
| 11G27CN | W P W W P W R R K |
| 11G28CN | R W W W P W R R K |
| 11H1CN | A L R W P W W P W R R K |
| 11H2CN | I A R W P W W P W R R K |
| 11H3CN | I L A W P W W P W R R K |
| 11H4CN | I L R A P W W P W R R K |
| 11H5CN | I L R W A W W P W R R K |
| 11H6CN | I L R W P A W P W R R K |
| 11H7CN | I L R W P W A P W R R K |
| 11H8CN | I L R W P W W A W R R K |
| 11H9CN | I L R W P W W P A R R K |
| 11H10CN | I L R W P W W P W A R K |
| 11H11CN | I L R W P W W P W R A K |
| 11H12CN | I L R W P W W P W R R A |
| 11J01CN | R R I W K P K W R L P K R |
| 11J02CN | W R W W K P K W R W P K W |
| 11J02ACN | W R W W K P K W R W P K W |
| 11J30CN | W R W W K V A W R W V K W |
| 11J32CN | Y R Y Y K P K Y R Y P K Y |
| 11J33CN | F R F F K P K F R F P K F |
| 11J36CN | W R W W K V W R W V K W |
| 11J38CN | W R W W K V V W R W V K W |
| 11J44CN | W R L L K L A L R L L K W |
| 11J45CN | L R F L K W A P R L W K L |
| 11J58CN | W (Orn) W W (Orn) V A W (Orn) W V (Orn) W |
| 11J67CN | W (Orn) W W (Orn) P (Orn) W (Orn) W P (Orn) W |
| 11J68CN | W (Dab) W W (Dab) P (Dab) W (Dab) W P (Dab) W |
| 11J84CN | H-L(Orn)FL(Orn)WAP(Orn)LW(Orn)L-CN |
| 11J97 | H-GWRFLKLAWRFLKL-OH |
| 11J105CN | H-LRFLKW(Aib)WRFLKL-CN |
| 11J115CN | H-RILRWVWRILR-CN |
| 11J131CN | H-ILRWVWRIL-CN |
| 11J136 | H-GWRFLKLAWRFLKLRR-OH |
| 11J148CN | H-ILRWVWRIL-CN |
| 11J157CN | H-RILRW(Aib)WRILR-CN |
| 21A1 | K K W W R R V L S G L K T A G P A I Q S V L N K |
| 21A2 | K K W W R R A L Q G L K T A G P A I Q S V L N K |
| 21A10 | K K W W R R V L K G L S S G P A L S N V |
| 22A1 | K K W W R R A L Q A L K N G L P A L I S |
| 26 | K W K S F I K K L T S A A K K V V T T A K P L I S S |
| 27 | K W K L F K K I G I G A V L K V L T T G L P A L I S |
| 28 | K W K L F K K I G I G A V L K V L T T G L P A L K L T K |
| 29 | K W K S P I K K L T T A V K K V L T T G L P A L I S |
| 29A2 | K W K S F I K N L T K V L K K V V T T A L P A L I S |
| 29A3 | K W K S P I K K L T S A A K K V L T T G L P A L I S |
| 29F1 | K W K L F I K K L T P A V K K V L L T G L P A L I S |
| 31 | G K P R P Y S P I P T S P R P I R Y |
| REWH 53A5 | R L A R I V V I R V A R |
| Nt-Acryloyl-11B7CN | |
| Nt-glucosyl-11J36CN | |
| Nt-glucosyl-11J38CN | |

Nt prefix = N-terminal modification
CN suffix = amidated C-terminus
A suffix = acetylated N-terminus
H suffix = homoserine at C-terminus
M suffix = MAP branched peptide
R suffix = retro-synthesized peptide
Orn = ornithine
Dab = 2,4-diamino butyric acid
Aib = aminoisobutyric acid
Upper case letter = L-enantiomer amino acid
Lower case letter = D-enantiomer amino acid

Example 2

Synthesis of Modified Peptides

Antimicrobial and/or anti-inflammatory peptides, such as indolicidin analogs or derivatives thereof, are modified to alter the physical properties of the original peptide, either by use of modified amino acids in synthesis or by post-synthetic modification. Such modifications include: acetylation at the N-terminus, Fmoc-derivatized N-terminus, polymethylation, peracetylation, and branched derivatives. Peptides modified using the procedures described herein are listed in Table 4.

α-N-Terminal Acetylation.

Prior to cleaving the peptide from the resin and deprotecting it, the fully protected peptide is treated with N-acetylimidazole in DMF for 1 h at room temperature, which results in selective reaction at the α-N-terminus. The peptide is then deprotected/cleaved and purified as for an unmodified peptide.

Fmoc-Derivatized α-N-Terminus.

If the final Fmoc deprotection step is not carried out, the α-N-terminus Fmoc group remains on the peptide. The peptide is then side-chain deprotected/cleaved and purified as for an unmodified peptide.

Polymethylation.

The purified peptide in a methanol solution is treated with excess sodium bicarbonate, followed by excess methyl iodide. The reaction mixture is stirred overnight at room temperature, extracted with organic solvent, neutralized and purified as for an unmodified peptide. Using this procedure, a peptide is not fully methylated; methylation of 11CN yielded an average of 6 methyl groups. Thus, the modified peptide is a mixture of methylated products.

Caprolactam Modification.

A purified peptide in DMF solution is cooled to 0° C. on ice with stirring. Added to the peptide solution is 2-(1H-benzotriazole-1-yl)-1,1,3,3-teramethyluronium hexafluorophosphate and N-methylmorpholine; the reaction mixture is removed from the ice bath and stirred for 1 h, until the reaction mix rises to room temperature. Water is added and the resulting caprolactam peptide solution is purified by C8 RP-HPLC.

Peracetylation.

A purified peptide in DMF solution is treated with N-acetylimidazole for 1 h at room temperature. The crude product is concentrated, dissolved in water, lyophilized, re-dissolved in water and purified as for an unmodified peptide. Complete acetylation of primary amine groups is observed.

Four/Eight Branch Derivatives.

The branched peptides are synthesized on a four- or eight-branched core bound to the resin. Synthesis and deprotection/cleavage proceed as for an unmodified peptide. These peptides are purified by dialysis against 4 M guanidine hydrochloride then water, and analyzed by mass spectrometry.

TABLE 2

Modified Indolicidin analogs and derivatives thereof

| Peptide modified | Peptide name | Modification |
|---|---|---|
| 10 | 10A | Acetylated α-N-terminus |
| 11 | 11A | Acetylated α-N-terminus |
| 11CN | 11ACN | Acetylated α-N-terminus |
| 11CN | 11CNW1 | Fmoc-derivatized N-terminus |
| 11CN | 11CNX1 | Polymethylated derivative |
| 11CN | 11CNY1 | Peracetylated derivative |
| 11 | 11M4 | Four branch derivative |
| 11 | 11M8 | Eight branch derivative |
| 11B1CN | 11B1CNW1 | Fmoc-derivatized N-terminus |
| 11B4CN | 11B4ACN | Acetylated N-terminus |
| 11B7CN | 11B7ACN | Acetylated N-terminus |
| 11B7CN | 11B7CNF12 | Formylated Lys[12] |
| 11B7 | 11B7Cap12 | Caprolactam Lys[12] |
| 11B9CN | 11B9ACN | Acetylated N-terminus |
| 11D9 | 11D9M8 | Eight branch derivative |
| 11D10 | 11D10M8 | Eight branch derivative |
| 11G6CN | 11G6ACN | Acetylated α-N-terminus |
| 11G7CN | 11G7ACN | Acetylated α-N-terminus |

Example 3

Antimicrobial Activity of Candidate Peptides and Analogs Thereof

A peptide may be tested tor antimicrobial activity by using an in vitro assay as described below.

Agarose Dilution Assay

The agarose dilution assay measures antimicrobial activity of peptides and peptide analogues. The activity is expressed as the minimum inhibitory concentration (MIC) in µg/ml of the peptide.

In order to mimic in vivo conditions, calcium and magnesium supplemented Mueller Hinton broth is used in combination with a low EEO agarose as the bacterial growth medium. Agarose, rather than agar, is used as the charged groups in agar prevent peptide diffusion through the medium. The medium is autoclaved, then cooled to 50-55° C. in a water bath before aseptic addition of a peptide solution. The same volume of different concentrations of peptide solution is added to the cooled, molten agarose that is then poured into a petri plate to a depth of 3-4 mm and allowed to solidify.

The bacterial inoculum is adjusted to a 0.5 McFarland turbidity standard (PML Microbiological) and then diluted 1:10 before application on to the agarose plate. The final inoculum applied to the agarose is approximately $10^4$ CFU in a 5-8 mm diameter spot. The agarose plates are incubated at 35-37° C. for 16 to 20 hours.

The MIC is recorded as the lowest concentration of peptide that completely inhibits growth of the organism as determined by visual inspection. Representative MIC values for various peptide analogues against bacteria and yeast are shown in Table 3.

TABLE 3

Antimicrobial activity of peptides as determined by agarose dilution susceptibility testing

| | | Minimum Inhibitory Concentration (μg/ml) | | | | | | |
|---|---|---|---|---|---|---|---|---|
| Organism | Strain # | 11B7CN | 11F4CN | 11F12CN | 11F17CN | 11F66CN | 11J02CN | 11J30CN |
| A. calcoaceticus | ACA002 | 4 | 4 | 1 | 1 | | 2 | 2 |
| E. cloacae | ECL007 | 128 | 64 | 32 | 16 | 8 | 128 | 16 |
| E. coli | ECO005 | 16 | 4 | 4 | 2 | 2 | 16 | 8 |
| K. pneumoniae | KPN001 | 128 | 4 | 8 | 2 | 2 | 32 | 2 |
| P. aeruginosa | PAE004 | 128 | 32 | 16 | 16 | 8 | 32 | 32 |
| S. maltophilia | SMA002 | 16 | 16 | 2 | 1 | 2 | 4 | 4 |
| S. marcescens | SMS003 | >128 | >128 | >128 | >128 | >128 | >128 | >128 |
| E. faecalis | EFS001 | 64 | 8 | 2 | 2 | 2 | 64 | 32 |
| S. aureus | SAU014 | 4 | 4 | 2 | 1 | 2 | 2 | 2 |
| S. epidermidis | SEP010 | 4 | 2 | 1 | 1 | 1 | 2 | 2 |
| S. mitis | SMT014 | 2 | 2 | 1 | 1 | 1 | 2 | 1 |
| S. pneumoniae | SPN002 | 4 | 8 | 4 | 1 | 2 | 8 | 2 |
| S. pyogenes | SPY001 | 1 | 2 | 0.5 | 0.5 | 1 | 1 | 2 |
| C. jeikeium | CJK005 | 0.5 | 2 | 0.5 | 0.5 | 1 | 1 | 0.5 |
| C. albicans | CAL002 | 16 | 32 | 16 | 32 | 16 | 16 | 16 |
| C. neoformans | CNE001 | 4 | 8 | 4 | 4 | 8 | 4 | 4 |

Example 4

Activity of Indolicidin Peptides on Cytokine Production

Human peripheral blood lymphocytes (PBLs) were collected from a healthy adult male and plated at $10^6$ cells/ml in serum free lymphocyte growth media in a 96-well plate. The PBLs were stimulated with 10 μg/ml PHA in the presence or absence of test sample and incubated at 37° C. at 5% $CO_2$ for 48 hours. Collected and pooled supernatants were stored at −20° C., then assayed with commercially available ELISA kits (Endogen and Biosource) and assayed for viability with LDH (Boehringer Mannheim). The cells remaining after supernatant removal were returned to the incubator and proliferation was determined at 72 hours by using Alamarblue (Alamar Bioscience). Compounds were tested at 1, 10, 100 and 1000 μg/ml. The peptides were effective at inhibiting cytokine production and PBL proliferation (Table 4), which indicates these peptides can function as anti-inflammatory agents.

Example 5

Indolicidin Peptides in Oxazolone Contact Hypersensitivity Model

CD-1 mice are treated with 3% oxazolone (Sigma) (30 mg/ml) in corn oil:acetone on a shaved abdomen. All solutions are sonicated for 7 minutes. Five days later, the mice are challenged with a 2% oxazolone (20 mg/ml) in acetone on the left ear, with the right ear being left untreated (control). One hour after challenge, the candidate peptide in a 70% EtOH/30% propylene glycol formulation (vehicle) was applied to the left ear, with the right ear being left untreated. After 24 h, 7 mm ear punches are taken from each ear of the mice. The ear punches are placed on a scale and the difference between the treated and untreated ears were compared. The percent inhibition of inflammation was calculated by comparing the mean of each treated group to the control group. The positive control is hydrocortisone (a known anti-inflammatory agent). Most of the indolicidin peptides inhibited inflammation as well as hydrocortisone.

TABLE 4

Inhibition of cytokine production in activated PBLs and PBL proliferation
$IC_{50}$ μg/ml

| ID | IL-1α | IL-2 | IL-4 | IL-6 | IL-10 | IL-12 | IFNγ | TNFα | Proliferation |
|---|---|---|---|---|---|---|---|---|---|
| 11B7CN | 550 | 110 | 45 | 380 | 17 | 50 | 70 | 26 | 42 |
| 11F17CN | 45 | >1000 | 220 | 500 | 18 | 120 | 93 | 70 | 410 |
| 11F61CN | 67 | 900 | >1000 | >1000 | 53 | 550 | 280 | 375 | >1000 |
| 11J02CN | 7 | >1000 | 115 | 510 | 23 | 34 | 45 | 34 | 81 |
| 11J30CN | 25 | >1000 | 65 | 4 | 33 | 26 | 28 | 36 | 55 |
| 11F43 | 18 | 640 | >1000 | 980 | 28 | 130 | 33 | 42 | 450 |
| 11F46CN | 6 | >1000 | 100 | 1 | 32 | 36 | 32 | 16 | 360 |
| 11F66CN | >1000 | 480 | >1000 | 1 | 40 | 280 | 125 | 110 | 120 |
| 11J37CN | 160 | 47 | 84 | 175 | 16 | 15 | 55 | 28 | 510 |
| 11F35CN | >1000 | 470 | 350 | 290 | 280 | 50 | 420 | 195 | 510 |
| 11F12CN | 500 | 570 | 325 | 140 | 30 | 120 | 250 | 68 | 480 |

TABLE 5

% Inhibition of Inflammation

| Compound* | Results† |
|---|---|
| Hydrocortisone | 84.92 |
| 11B7CN | 78.33 |
| 11F17CN | 71.60 |
| 11F61CN | 72.82 |
| 11J02CN | 58.12 |
| 11J30CN | 94.15 |
| 11F43 | 82.63 |
| 11F46CN | 55.25 |
| 11F66CN | 79.85 |
| 11J37CN | 44.26 |
| 11F35CN | 77.89 |
| 11F12CN | 86.50 |

*Dosage of 0.1%
†% Inhibition

Example 6

Anti-Inflammatory Activity of Indolicidin Peptides in TPA Ear Edema Model

To investigate the anti-inflammatory effect of topically and systemically applied candidate peptides, a mouse model of ear inflammation induced by 12-o-tetradecanoyl phorbol acetate (TPA) was used. Ear edema is induced by topical application of TPA. The candidate peptide is applied topically or systemically at various concentrations in a suitable formulation immediately after TPA application. $ED_{50}$ is determined with ear biopsy weight used as an end point. Edematous response is due to increased vascular permeability mediated by release of prostaglandins, histamine and serotonin. Anti-inflammatory compounds including glucocorticoids and non-steroid anti-inflammatory drugs (NSAIDs), reduce edema by inhibiting the action of several enzymes including cyclooxygenase, an enzyme involved in synthesis of prostaglandins.

Male Swiss CD1 mice weighing between 24 to 37 grams and between 5-6 weeks of age were used in the study. A 0.005% (w/v) solution of TPA in acetone was prepared. Indolicidin analogs were prepared at 0.1%, 1.0%, and 5.0% in 95% ethanol or 50% ethanol, 5 mM lactic acid-sodium lactate buffer, pH 4.0. Anti-inflammatory activity was compared to dexamethasone and erythromycin. The animals in the control group were treated with 20 µl of 0.005% TPA solution administered as a single topical application to the dorsal area of the right ear. Animals in the formulation (vehicle) group were treated with 20 µl of 0.005% TPA solution, followed immediately by topical application of 20 µl of formulation vehicle to the same ear. The animals in the peptide composition group were treated with 20 µl of 0.005% TPA solution followed immediately by topical application of the selected peptide composition to the same ear. The animals in positive control group were treated with 20 µl of 0.005% TPA solution followed immediately by topical application of dexamethasone or erythromycin solution to the same ear. The left ear in all groups was left untreated and used as a control. Six hours after administration of the various treatments, all animals were euthanized by $CO_2$ gas inhalation. Both ears were removed and skin biopsies were obtained using a dermal biopsy punch. The biopsy samples were weighed and the difference in biopsy weights between the right and left ears was calculated. Data were analyzed by using ANOVA (One-way analysis of variance) followed by Dunnet's multiple comparison test.

TABLE 6

Inhibition of TPA-Induced Ear Edema by Candidate Peptides.

| Peptide | Sequence | Topical Dose (% change vs. vehicle) | | | Systemic Dose (% change vs. vehicle) |
|---|---|---|---|---|---|
| | | 0.1% | 1.0% | 5.0% | 5 mg/kg |
| 11D21CN | ILRWPWWPWRRKhs-CN | | +32* | -27* | |
| R11B7HCN | ILRWPWWPWRRKhs-CN | | +27* | -56* | |
| 11B7CN | ILRWPWWPWRRK-CN | -10 | -9 | -60 | |
| | | | -16* | -35* | |
| 11B24ACN | A-ILRWPWWPWTTT-CN | | | -75 | |
| 11B11CN | ILEEWPWWPWEEE-CN | | | -64* | |
| 11B24CN | ILTWPWWPWTTT-CN | | -32 | -64 | |
| 11B38CN | ILQWPWWPWQQQ-CN | | -8 | -51 | |
| 11F4CN | ILRWVWWVWRRK-CN | | | -55 | |
| 11F11CN | RLWVWWVW-CN | | -49* | -75* | |
| | | | | -87 | |
| 11F12CN | RLWVWWVWRRK-OH | | | -56 | |
| 11F60CN | RLWWQQWWRR-CN | | | -41 | |
| 11F65CN | RLWVVVVWRR-CN | | | -94 | -15 |

TABLE 6-continued

Inhibition of TPA-Induced Ear Edema by Candidate Peptides.

| Peptide | Sequence | Topical Dose (% change vs. vehicle) | | | Systemic Dose (% change vs. vehicle) |
|---|---|---|---|---|---|
| | | 0.1% | 1.0% | 5.0% | 5 mg/kg |
| 11F66CN | RLVVWVVWRR-CN | -17* | -64* | -81* | |
| 11F82CN | RLLVWWVLRR-CN | | -62 | | |
| 11F83CN | RLGGGGGGRR-CN | | -28 | | |
| 11F110 | RLVVWVVWRRK-OH | -45* | -83* | -87* | |
| 11J02CN | WRWWKPKWRWPKW-CN | | -44 | | |
| 11J30CN | WRWWKVAWRWVKW-CN | | -26 | | |
| 11J32CN | YRYYKPKTRYPKY-CN | | -30 | | |
| 11J33CN | PRFFKPKFRFPKF-CN | | -52 | | |
| 11J44CN | WRLLKLALRLLKW-CN | | -88 | | -32 |
| 11J45CN | LRFLKWAFRLWKL-CN | | -69 | | |
| 11J67CN | H-W(Orn)WW(Orn)P(Orn)W(Orn)WP(Orn)W-CN | | -33* | -66* | |
| 11J68CN | H-W(Dab)WW(Dab)P(Dab)W(Dab)WP(Dab)W-CN | | -55* | -85* | |
| 11J84CN | H-L(Orn)FL(Orn)WAF(Orn)LW(Orn)L-CN | -14 | -35 | | |
| 11J97 | H-GWRFLKLAWRFLKL-OH | +33 | -29 | | -49 |
| 11J105CN | H-LRFLKW(Aib)WRFLKL-CN | -4 | -51 | | |
| 11J115CN | H-RILRWVWRILR-CN | -1 | -57 | | |
| 11J131CN | H-ILRWVWRILR-CN | -20 | -43 | | |
| 11J136 | H-GWRFLKLAWRFLKLRR-OH | -12 | -54 | | |
| 11J148CN | H-ILRWVWRIL-CN | -33 | -74 | | |
| 11J157CN | H-RILRW(Aib)WRILR-CN | +5 | -55 | | |
| Erythromycin | | -20* | -67* | -87* | |
| Dexamethasone | | -92 >-90* | | | >-80 |

Candidate peptides were formulated in 95% ethanol or 50% ethanol/5 mM lactate buffer*.

Most indolicidin analogs and derivatives, when applied systematically, or topically to the mouse ear, significantly inhibited TPA-induced ear edema (p<0.001) in a dose dependent manner (Table 6). Therefore, these indolicidin analogs and derivatives exhibit a significant anti-inflammatory activity.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for preventing the recurrence of inflammation in a subject in need thereof, comprising administering to the subject an anti-inflammatory peptide of up to 35 amino acids comprising 11B7 (SEQ ID NO: 23), wherein the inflammation is caused by a condition other than a microbial infection.

2. The method according to claim 1, wherein the anti-inflammatory peptide is at a concentration of about 0.01% to about 10%.

3. The method according to claim 2, wherein the anti-inflammatory peptide is at a concentration of about 0.5% to about 5%.

4. The method according to claim 3, wherein the anti-inflammatory peptide is at a concentration of about 1% to about 3%.

5. The method according to claim 1, wherein the inflammation is selected from the group consisting of acute, adhesive, atrophic, catarrhal, chronic, croupous, degenerative, exudative, fibrinopurulent, fibrinous, granulomatous, interstitial, intraepithelial, necrotic, proliferative, pseudomembranous, purulent, sclerosing, serofibrinous, serous, and subacute.

6. The method according to claim 1, wherein the condition is selected from the group consisting of arthritis, autoimmune disease, burn, Crohn's disease, contact hypersensitivity, delayed type hypersensitivity, eczema, fibromyositis, graft rejection, lichen, multiple sclerosis, parapsoriasis, and sclerosis.

7. The method according to claim 1, wherein the inflammation is associated with a medical device.

8. The method according to claim 1, wherein the anti-inflammatory peptide is administered in combination with an anti-inflammatory agent.

9. The method according to claim 1, wherein the peptide has one or more amino acids altered to a corresponding D-amino acid.

10. The method according to claim 1, wherein the peptide is amidated at the C-terminal amino acid.

11. The method according to claim 1, wherein the peptide is acetylated at the N-terminal amino acid.

12. The method according to claim 1, wherein the administration is topical.

13. The method according to claim 1, wherein the peptide is administered to a mucosa.

14. A method for preventing inflammation in a subject in need thereof, comprising administering to the subject an anti-inflammatory peptide of up to 35 amino acids comprising 11B7 (SEQ ID NO: 23), wherein the inflammation is caused by a condition other than a microbial infection.

15. The method according to claim 14, wherein the inflammation is a recurrent lesion.

16. The method according to claim 14, wherein the anti-inflammatory peptide is at a concentration of about 0.01% to about 10%.

17. The method according to claim 16, wherein the anti-inflammatory peptide is at a concentration of about 0.5% to about 5%.

18. The method according to claim 17, wherein the anti-inflammatory peptide is at a concentration of about 1% to about 3%.

19. The method according to claim 14, wherein the inflammation is selected from the group consisting of acute, adhesive, atrophic, catarrhal, chronic, croupous, degenerative, exudative, fibrinopurulent, fibrinous, granulomatous, interstitial, intraepithelial, necrotic, proliferative, pseudomembranous, purulent, sclerosing, serofibrinous, serous, and subacute.

20. The method according to claim 14, wherein the condition is selected from the group consisting of arthritis, autoimmune disease, burn, Crohn's disease, contact hypersensitivity, delayed type hypersensitivity, eczema, fibromyositis, graft rejection, lichen, multiple sclerosis, parapsoriasis, and sclerosis.

21. The method according to claim 14, wherein the inflammation is associated with a medical device.

22. The method according to claim 14, wherein the anti-inflammatory peptide is administered in combination with an anti-inflammatory agent.

23. The method according to claim 14, wherein the peptide has one or more amino acids altered to a corresponding D-amino acid.

24. The method according to claim 14, wherein the peptide is amidated at the C-terminal amino acid.

25. The method according to claim 14, wherein the peptide is acetylated at the N-terminal amino acid.

26. The method according to claim 1, wherein the administration is topical.

27. The method according to claim 1, wherein the peptide is administered to a mucosa.

* * * * *